United States Patent [19]

Hosoi et al.

[11] Patent Number: 4,839,353

[45] Date of Patent: Jun. 13, 1989

[54] ANTI-ULCER SUBSTITUTED PYRIDINE DERIVATIVES

[75] Inventors: Masaaki Hosoi, Kawasaki; Ryo Nishioka, Ichikawa; Yoshio Hioki; Yoshiaki Iida, both of Yokohama; Hiroshi Takeshita, Ichikawa; Kenji Niiyama, Ichikawa; Yusuke Hidaka, Tokyo, all of Japan

[73] Assignee: Banyu Pharmaceutical Co., Ltd., Tokyo, Japan

[21] Appl. No.: 110,369

[22] Filed: Oct. 20, 1987

[30] Foreign Application Priority Data

Oct. 21, 1986 [JP] Japan .................................. 61-248363
Aug. 10, 1987 [JP] Japan .................................. 62-199597

[51] Int. Cl.$^4$ ...................... A61K 31/55; C07D 401/04
[52] U.S. Cl. .................................. 514/212; 514/227.8; 514/235.5; 514/252; 514/277; 514/318; 514/343; 514/345; 514/349; 514/350; 514/351; 514/352; 514/354; 514/355; 514/357; 540/597; 544/58.6; 544/60; 544/124; 544/131; 544/360; 544/365
[58] Field of Search ................ 540/512, 597; 544/124, 544/58.6, 60, 131, 360, 365; 546/193, 194, 229, 336, 329, 334, 335, 281, 297, 298, 300, 290, 301, 302, 303, 307, 310, 304, 312, 314, 315, 340, 343, 344; 514/212, 227, 318, 345, 357, 252, 227.8, 235.5, 227, 343, 349, 350, 351, 352, 354, 355

[56] References Cited

U.S. PATENT DOCUMENTS

| | | | |
|---|---|---|---|
| 3,661,917 | 5/1972 | Kaiser et al. ...................... | 546/340 X |
| 3,840,547 | 10/1974 | Mendelson ....................... | 546/339 X |
| 3,998,955 | 12/1976 | Kuhnis et al. ..................... | 514/350 |
| 4,018,910 | 4/1977 | Winter et al. ..................... | 546/340 X |
| 4,104,274 | 8/1978 | Connor et al. .................... | 546/340 X |
| 4,337,259 | 6/1982 | Crossley ........................ | 546/339 X |

FOREIGN PATENT DOCUMENTS

4512319  5/1970  Japan .................................. 546/339

OTHER PUBLICATIONS

*Chemical Abstracts,* 72:4337g (1970) [AL-Tai, F et al. *Bull Coll. Sci., Univ. Baghdad* 1967, 10, 81–92].
*Chemical Abstracts,* Subject Index, 8th Coll. Index, p. 26476s.
*Chemical Abstracts,* 73:14702z (1970) [Miyano, S., Japan 7011, 500, 4/25/70].
*Chemical Abstracts,* 75: 129617j (1971) [Baker, B. et al., *J. Med. Chem.,* 1971, 14(9), 793–799].
*Chemical Abstracts,* 103:104926t (1985) [Zhang, Z. et al., *Yoyao Gongye,* 1985, 16(3), 113–116].

Primary Examiner—Richard A. Schwartz
Attorney, Agent, or Firm—Sherman & Shalloway

[57] ABSTRACT

A substituted pyridine derivative represented by the general formula

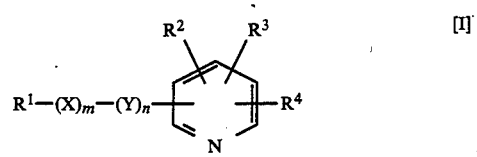

wherein $R^1$ represents a phenyl or naphthyl group which may optionally be substituted by a substituent selected from the class consisting of a hydroxyl group, lower alkyl groups, lower alkoxy groups, cycloalkyl groups, lower alkoxycarbonyl groups, a phenyl group and halogen atoms; X represents an oxygen atom, a sulfur atom, a carbonyl group, or a group of the formula —CH(OH)— or —N($R^a$)— in which $R^a$ is a hydrogen atom or a lower alkyl group; Y represents a linear or branched lower alkylene group or a vinylene group which may optionally be substituted by a lower alkyl group, with the proviso that when X is an oxygen or sulfur atom, Y represents the lower alkylene group; $R^2$ and $R^3$ are identical or different and each represents a hydrogen atom or a lower alkyl group; $R^4$ represents a hydrogen atom, a lower alkoxy group, a cycloalkyloxy group, a lower alkylthio group, a cycloalkylthio group, an aryloxy group, an aralkyloxy groups or a group of the formula

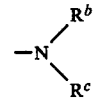

in which $R^b$ and $R^c$ are identical or different and each represents a hydrogen atom or a lower alkyl group. or $R^b$ and $R^c$, taken together, may form together with the adjacent nitrogen atom a 5- to 7-membered saturated heterocyclic ring which may optionally contain at least one additional hetero atom selected from the group consisting of oxygen, sulfur and nitrogen atoms and may optionally be substituted by a lower alkyl group; m and n are each 0 or 1, with the proviso that m and n are not 0 at the same time, or an acid addition salt thereof. This compound is useful as an antiulcer agent.

7 Claims, No Drawings

ANTI-ULCER SUBSTITUTED PYRIDINE DERIVATIVES

This invention relates to new pyridine compounds, and more specifically, to novel substituted pyridine derivatives which are very effective for the treatment of gastric or duodenal ulcer in mammals and to the use of these pyridine derivatives as an antiulcer agent.

One method of treating gastrointestinal diseases, particularly gastric and duodenal ulcers, is to administer drugs having gastric acid antisecretory activity. One example of the drugs used is cimetidine (see Merck Index, 10th Edition, Monograph No. 2254) which is a histamine $H_2$ antagonist. It was recently found that in the parietal cells, $H^+,K^+$-ATPase having the property of being activated with a potassium ion governs gastric acid secretion and an inhibitor of this enzyme can also be a useful gastric acid secretion inhibitor (see Nature, 290, 159–161, 1981). Benzimidazole derivatives typified by omeprazole (see European Pat. No. 5129 and U.S. Pat. Nos. 4,337,257 and 4,508,905) and benzoxazole derivatives (see European Patent Publication No. 45,200) are known as compounds having inhibitory activity on $H^+,K^{30}$-ATPase.

We have synthesized and studied various compounds with a view to finding compounds having excellent properties as an antiulcer agent. Consequently, we have found novel substituted pyridine derivatives having excellent gastric acid antisecretory activity and gastric mucosa protecting activity, as shown by Pharmacological Test Example given hereinbelow.

Thus, according to this invention, there are provided substituted pyridine derivatives represented by the general formula

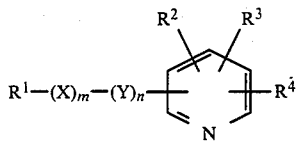

wherein $R^1$ represents a phenyl or naphthyl group which may optionally be substituted by a substituent selected from the class consisting of a hydroxyl group, lower alkyl groups, lower alkoxy groups, cycloalkyl groups, lower alkoxycarbonyl groups, a phenyl group and halogen atoms; X represents an oxygen atom, a sulfur atom, a carbonyl group, or a group of the formula —CH(OH)— or —N($R^a$)— in which $R^a$ is a hydrogen atom or a lower alkyl group; Y represents a linear or branched lower alkylene group or a vinylene group which may optionally be substituted by a lower alkyl group, with the proviso that when X is an oxygen or sulfur atom, Y represents the lower alkylene group; $R^2$ and $R^3$ are identical or different and each represents a hydrogen atom or a lower alkyl group; $R^4$ represents a hydrogen atom, a lower alkoxy group, a cycloalkyloxy group, a lower alkylthio group, a cycloalkylthio group, an aryloxy group, an aralkyloxy group or a group of the formula

in which $R^b$ and $R^c$ are identical or different and each represents a hydrogen atom or a lower alkyl group, or $R^b$ and $R^c$, taken together, may form together with the adjacent nitrogen atom a 5- to 7-membered saturated heterocyclic ring which may optionally contain at least one additional hetero atom selected from the group consisting of oxygen, sulfur and nitrogen atoms and may optionally be substituted by a lower alkyl group; m and n are each 0 or 1, with the proviso that m and n are not 0 at the same time, and acid addition salts thereof.

In the present specification and the appended claims, the term "lower" used to qualify a group or a compound means that the group or compound so qualified has not more than 6, preferably not more than 4, carbon atoms.

The lower alkyl group may be linear or branched, and includes, for example, methyl, ethyl, propyl, isopropyl, butyl, sec-butyl, tert-butyl, pentyl, isopentyl and sec-pentyl groups. The lower alkoxy group is a lower alkyl—O— group in which the lower alkyl moiety has the above meaning, and examples include methoxy, ethoxy, propoxy, isopropoxy, butoxy, isobutoxy, tert-butoxy, pentyloxy, isopentyloxy, neopentyloxy and tert-pentyloxy groups. The cycloalkyloxy group includes cycloalkyloxy groups having 3 to 8 carbon atoms, preferably 5 to 8 carbon atoms, such as cyclopentyloxy, cyclohexyloxy and 4-methylcyclohexyloxy groups. The lower alkylthio group is a lower alkyl—S— group in which the lower alkyl moiety has the above meaning, and examples include methylthio, ethylthio, propylthio, isopropylthio, butylthio, isobutylthio, tert-butylthio, pentylthio, isopentylthio, neopentylthio and tert-pentylthio groups. The cycloalkylthio group includes cycloalkylthio groups having 3 to 8 carbon atoms, preferably 5 to 8 carbon atoms, such as cyclopentylthio and cyclohexylthio groups.

The aryloxy group is an aryl—O— group in which the aryl moiety has the following meaning. The aryl moiety (group) is mononuclear or polynuclear, and includes, for example, phenyl, 1-naphthyl and 1-naphthyl groups. The aryl group may optionally have 1 to 4, preferably 1 or 2, substituents on the aromatic ring. Examples of the substituents are lower alkyl groups, lower alkoxy groups, lower alkoxycarbonyl groups, lower haloalkyl groups and halogen atoms. Examples of the aryloxy group thus include phenoxy, 4-methylphenoxy, 4-methoxyphenoxy, 4-chlorophenoxy, 1-naphthoxy and 2-naphthoxy groups.

The aralkyloxy group is an aralkyl—O— group in which the aralkyl moiety or group is an aryl-substituted lower alkyl group with the aryl moiety and the lower alkyl moiety having the above-mentioned meanings. Examples of the aralkyl group are benzyl, 4-methylbenzyl, 4-methoxybenzyl, phenethyl, 4-methoxyphenethyl, 1-naphthylmethyl and 2-naphthylmethyl groups. Thus, examples of the aralkyloxy group include benzyloxy, 4-methylbenzyloxy, 4-methoxybenzyloxy, 1-naphthylmethyloxy and 2-naphthylmethyloxy groups.

The lower alkoxycarbonyl group is a lower alkyl—O—CO— group in which the lower alkyl moiety has the above meaning, and examples include methoxy-carbonyl, ethoxycarbonyl, propoxycarbonyl and isopropoxycarbonyl groups.

The halogen atoms include fluorine, chlorine, bromine and iodine atoms.

In the group represented by

$R^b$ and $R^c$ are identical or different and each represents a hydrogen atom or a lower alkyl group, or taken together $R^b$ and $R^c$ may form a 5- to 7-membered saturated heterocyclic ring together with the adjacent nitrogen atom. The saturated heterocyclic ring may optionally contain at least one additional hetero atom selected from the group consisting of oxygen, sulfur and nitrogen atoms and may be substituted by a lower alkyl group. Examples of the group

include amino, methylamino, ethylamino, dimethylamino, diethylamino, N-methyl-N-ethylamino, and saturated heterocyclic groups such as 1-pyrrolidinyl, piperidino, 3-methylpiperidino, 4-methylpiperidino, perhydroazepin-1-yl, morpholino, piperazin-1-yl, 4-methylpiperazin-1-yl and thiomorpholino groups.

The linear or branched lower alkylene group includes methylene, methylmethylene, ethylene, methylethylene and trimethylene groups. Examples of the vinylene groups which may optionally be substituted by a lower alkyl group are vinylene and methylvinylene groups.

In formula (I), in the substituted phenyl or naphthyl group represented by $R^1$, the number of substituents on the aromatic ring may be 1 to 4, preferably 1 or 2.

A preferred group of compounds among the compounds of formula (I) provided by this invention are compounds represented by the following formula

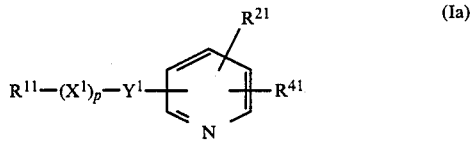

wherein $R^{11}$ represents a phenyl or naphthyl group which may optionally be substituted by one or two substituents selected from hydroxyl, $C_{1-4}$ alkyl, $C_{1-4}$ alkoxy, $C_{5-8}$ cycloalkyl, $C_{1-4}$ alkoxycarbonyl and phenyl groups and halogen atoms; $X^1$ represents an oxygen or sulfur atom; $Y^1$ represents a methylene, ethylene or vinylene group; p is 0 or 1, with the proviso that when p is 0, $Y^1$ is an ethylene or vinylene group, and when p is 1, $Y^1$ is a methylene group; $R^{21}$ represents a hydrogen atom or a $C_{1-4}$ alkyl group; $R^{41}$ represents a $C_{1-4}$ alkoxy group, a $C_{5-8}$ cycloalkyloxy group, a phenyloxy group, a benzyloxy group, a phenethyloxy group, or a pyrrolidin-1-yl, piperidino, perhydroazepin-1-yl, piperazin-1-yl or morpholino group which may optionally be substituted by a $C_{1-4}$ alkyl group.

A more preferred group of compounds of formula (I) are compounds of the following formula

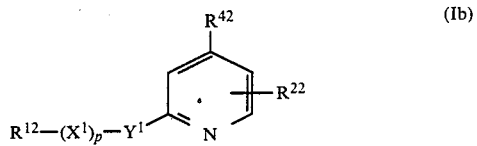

wherein $R^{12}$ represents a phenyl or naphthyl group which may optionally be substituted by one or two substituents selected from $C_{1-4}$ alkyl groups, $C_{5-8}$ cycloalkyl groups and halogen atoms; $X^1$ represents an oxygen or sulfur atom; $Y^1$ represents a methylene, ethylene or vinylene group; p is 0 or 1, with the proviso that when p is 0, $Y^1$ is an ethylene or vinylene group, and when p is 1, $Y^1$ is a methylene group; $R^{22}$ represents a $C_{1-4}$ alkyl group; $R^{42}$ represents a hydrogen atom, a cyclohexyloxy group or a piperidino, piperazin-1-yl or perhydroazepin-1-yl group which may optionally be substituted by a $C_{1-4}$ alkyl group.

It should be understood that when Y in the compounds of formula (I) is a vinylene group, the compounds of this invention include both E- and Z-isomers, and that the compounds of this invention include both types of isomers.

Typical examples of the compounds of formula (I) provided by this invention are listed below.

(1) 5-methyl-2-[(1-naphthyl)oxymethyl]-4-piperidinopyridine (2) 5-ethyl-2-[(1-naphthyl)oxymethyl]-4-piperidinopyridine (3) 5-methyl-2-[(2-naphthyl)oxymethyl]-4-piperidinopyridine (4) 5-methyl-2-phenoxymethyl-4-piperidinopyridine (5) 5-methyl-2-[(2,3-dichlorophenoxy)methyl]-4-piperidinopyridine (6) 2-[(4-tert-butylphenoxy)methyl]-5-methyl-4-piperidinopyridine (7) 2-[(4-sec-butylphenoxy)methyl]-5-methyl-4-piperidinopyridine (8) 2-[(4-cyclopentylphenoxy)methyl]-5-methyl-4-piperidinopyridine (9) 2-[(4-cyclohexylphenoxy)methyl]-4-piperidinopyridine

(10) 2-[(4-cyclohexylphenoxy)methyl]-5-methyl-4-piperidinopyridine

(11) 2-[(4-biphenylyl)oxymethyl]-5-methyl-4-piperidinopyridine

(12) 2-[(4-biphenylyl)oxymethyl]-4-methoxy-5-methylpyridine

(13) 2-anilinomethyl-5-methyl-4-piperidinopyridine

(14) 2-[(N-methylanilino)methyl]-5-methyl-4-piperidinopyridine

(15) 2-[(N-ethylanilino)methyl]-5-methyl-4-(perhydroazepin-2-yl)pyridine

(16) 5-methyl-2-phenylthiomethyl-4-piperidinopyridine

(17) 5-methyl-2-[(2,3-dimethylphenyl)thiomethyl]-4-piperidinopyridine

(18) 5-methyl-2-[(2-naphthyl)thiomethyl]-4-piperidinopyridine

(19) (E)-5-methyl-2-[2-(1-naphthyl)vinyl]-4-piperidinopyridine

(20) (Z)-5-methyl-2-[2-(1-naphthyl)vinyl]-4-piperidinopyridine

(21) (E)-2-[2-(2-methoxy-1-naphthyl)vinyl]-5-methyl-4-piperidinopyridine

(22) (E)-2-[2-(4-methyl-1-naphthyl)vinyl]-5-methyl-4-piperidinopyridine

(23) (Z)-2-[2-(4-methyl-1-naphthyl)vinyl]-5-methyl-4-piperidinopyridine

(24) (E)-2-[2-(4-chloro-1-naphthyl)vinyl]-5-methyl-4-piperidinopyridine

(25) (E)-5-ethyl-2-[2-(4-chloro-1-naphthyl)-vinyl]-4-piperidinopyridine

(26) (Z)-2-[2-(4-chloro-1-naphthyl)vinyl]-5-methyl-4-piperidinopyridine

(27) (Z)-5-ethyl-2-[2-(4-chloro-1-naphthyl)-vinyl]-4-piperidinopyridine

(28) (E)-2-[2-(4-fluoro-1-naphthyl)vinyl]-5-methyl-4-piperidinopyridine

(29) (Z)-2-[2-(4-fluoro-1-naphthyl)vinyl]-5-methyl-4-piperidinopyridine

(30) (Z)-2-[2-(4-fluoro-1-naphthyl)vinyl]-5-methyl-4-(perhydroazepin-1-yl)pyridine

(31) (E)-2-[2-(4-methoxy-1-naphthyl)vinyl]-5-methyl-4-piperidinopyridine (32) (Z)-2-[2-(4-methoxy-1-naphthyl)vinyl]-5-methyl-4-piperidinopyridine

(33) (E)-2-[2-(5-methyl-1-naphthyl)vinyl]-5-methyl-4-piperidinopyridine

(34) (Z)-2-[2-(5-methyl-1-naphthyl)vinyl]-5-methyl-4-piperidinopyridine

(35) (E)-2-[2-(5-methoxy-1-naphthyl)vinyl]-5-methyl-4-piperidinopyridine

(36) (Z)-2-[2-(5-methoxy-1-naphthyl)vinyl]-5-methyl-4-piperidinopyridine

(37) (E)-2-[2-(7-methoxy-1-naphthyl)vinyl]-5-methyl-4-piperidinopyridine

(38) (Z)-5-ethyl-2-[2-(8-methyl-1-naphthyl)vinyl]-4-piperidinopyridine

(39) (E)-2-[2-(8-methyl-1-naphthyl)vinyl]-5-methyl-4-piperidinopyridine

(40) (Z)-2-[2-(8-methyl-1-naphthyl)vinyl]-5-methyl-4-piperidinopyridine

(41) (Z)-2-[2-(8-methyl-1-naphthyl)vinyl]-5-methyl-4-(perhydroazepin-1-yl)pyridine

(42) (E)-5-methyl-2-[2-(1-naphthyl)vinyl]-pyridine

(43) (Z)-5-methyl-2-[2-(1-naphthyl)vinyl]-pyridine

(44) (E)-4-methoxy-5-methyl-2-[2-(1-naphthylvinyl]-pyridine

(45) (Z)-4-methoxy-5-methyl-2-[2-(1-naphthyl)vinyl]-pyridine

(46) (E)-5-methyl-2-[2-(1-naphthyl)vinyl]-4-propoxypyridine

(47) (Z)-5-methyl-2-[2-(1-naphthyl)vinyl]-4-propoxypyridine

(48) (E)-4-isopentyloxy-5-methyl-2-[2-(1-naphthyl)-vinyl]pyridine

(49) (Z)-4-isopentyloxy-5-methyl-2-[2-(1-naphthyl)-vinyl]pyridine

(50) (E)-5-methyl-2-[2-(1-naphthyl)vinyl]-4-pentyloxypyridine

(51) (Z)-5-methyl-2-[2-(1-naphthyl)vinyl]-4-pentyloxypyridine

(52) (Z)-5-methyl-2-[2-(1-naphthyl)vinyl]-4-hexyloxypyridine

(53) (E)-4-cyclohexyloxy-5-methyl-2-[2-(1-naphthyl)-vinyl]pyridine

(54) (Z)-4-cyclohexyloxy-5-methyl-2-[2-(1-naphthyl)-vinyl]pyridine

(55) (E)-5-methyl-2-[2-(1-naphthyl)vinyl]-4-phenoxypyridine

(56) (Z)-5-methyl-2-[2-(1-naphthyl)vinyl]-4-phenoxypyridine

(57) (E)-4-benzyloxy-5-methyl-2-[2-(1-naphthyl)-vinyl]pyridine

(58) (Z)-4-benzyloxy-5-methyl-2-[2-(1-naphthyl)-vinyl]pyridine

(59) (E)-4-[(4-methylbenzyl)oxy]-5-methyl-2-[2-(1-naphthyl)vinyl]pyridine

(60) (E)-5-methyl-2-[2-(1-naphthyl)vinyl]-4-phenethyloxypyridine

(61) (Z)-5-methyl-2-[2-(1-naphthyl)vinyl]-4-phenethyloxypyridine

(62) (E)-4-cyclohexylthio-5-methyl-2-[2-(1-naphthyl)vinyl]pyridine

(63) (Z)-4-cyclohexylthio-5-methyl-2-[2-(1-naphthyl)vinyl]-4-piperidinopyridine

(64) (E)-4-dimethylamino-5-methyl-2-[2-(1-naphthyl)vinyl]-4-piperidinopyridine

(65) (Z)-4-dimethylamino-5-methyl-2-[2-(1-naphthyl)vinyl]-4-piperidinopyridine

(66) (E)-5-methyl-2-[2-(1-naphthyl)vinyl]-4-(pyrrolidin-1-yl)pyridine

(67) (Z)-5-methyl-2-[2-(1-naphthyl)vinyl]-4-(pyrrolidin-1-yl)pyridine

(68) (E)-5-methyl-4-morpholino-2-[2-(1-naphthyl)-vinyl]pyridine

(69) (Z)-5-methyl-4-morpholino-2-[2-(1-naphthyl)-vinyl]pyridine

(70) (Z)-5-methyl-4-thiomorpholino-2-[2-(1-naphthyl)vinyl]pyridine

(71) (E)-5-methyl-4-(4-methylpiperazin-1-yl)-2-[2-(1-naphthyl)vinyl]pyridine

(72) (Z)-5-methyl-4-(4-methylpiperazin-1-yl)-2-[2-(1-naphthyl)vinyl]pyridine

(73) (E)-5-methyl-[2-(1-naphthyl)vinyl]-4-(perhydroazepin-1-yl)pyridine

(74) (Z)-5-methyl-[2-(1-naphthyl)vinyl]-4-(perhydroazepin-1-yl)pyridine

(75) (Z)-5-ethyl-[2-(1-naphthyl)vinyl]-4-(perhydroazepin-1-yl)pyridine

(76) (E)-5-methyl-4-(4-methylpiperidino)-2-[2-(1-naphthyl)vinyl]pyridine

(77) (Z)-5-methyl-4-(4-methylpiperidino)-2-[2-(1-naphthyl)vinyl]pyridine

(78) (Z)-5-methyl-4-(4-methylpiperidino)-2-[2-(8-methyl-1-naphthyl)vinyl]pyridine

(79) (E)-5-methyl-4-(3-methylpiperidino)-2-[2-(1-naphthyl)vinyl]pyridine

(80) (Z)-5-methyl-4-(3-methylpiperidino)-2-[2-(1-naphthyl)vinyl]pyridine

(81) (Z)-5-methyl-4-(3-methylpiperidino)-2-[2-(8-methyl-1-naphthyl)vinyl]pyridine

(82) (E)-4-diethylamino-5-methyl-2-[2-(1-naphthyl)-vinyl]pyridine

(83) (Z)-4-diethylamino-5-methyl-2-[2-(1-naphthyl)-vinyl]pyridine

(84) (E)-2-[2-(1-naphthyl)vinyl]-4-piperidinopyridine

(85) (Z)-2-[2-(1-naphthyl)vinyl]-4-piperidinopyridine

(86) (E)-5-ethyl-2-[2-(1-naphthyl)vinyl]-4-piperidinopyridine

(87) (Z)-5-ethyl-2-[2-(1-naphthyl)vinyl]-4-piperidinopyridine

(88) (Z)-5-ethyl-2-[2-(8-methyl-1-naphthyl)-vinyl]-4-(4-methylpiperidino)pyridine

(89) (E)-2-[2-(1-naphthyl)vinyl]-4-piperidino-5-propylpyridine

(90) (Z)-2-[2-(1-naphthyl)vinyl]-4-piperidino-5-propylpyridine

(91) (E)-3-[2-(1-naphthyl)vinyl]-2-piperidinopyridine
(92) (Z)-3-[2-(1-naphthyl)vinyl]-2-piperidinopyridine
(93) (E)-4-[2-(1-naphthyl)vinyl]-2-piperidinopyridine
(94) (E)-6-methyl-2-[2-(1-naphthyl)vinyl]-4-piperidinopyridine
(95) (Z)-6-methyl-2-[2-(1-naphthyl)vinyl]-4-piperidinopyridine
(96) (E)-3-[2-(2-naphthyl)vinyl]-4-piperidinopyridine
(97) (Z)-3-[2-(2-naphthyl)vinyl]-4-piperidinopyridine
(98) (E)-2-[2-(2-naphthyl)vinyl]-6-piperidinopyridine
(99) (Z)-2-[2-(2-naphthyl)vinyl]-6-piperidinopyridine
(100) (E)-2-[2-(4-biphenylyl)vinyl]-5-methyl-4-piperidinopyridine
(101) (Z)-2-[2-(2-biphenylyl)vinyl]-5-methyl-4-piperidinopyridine
(102) (Z)-2-[2-(4-biphenylyl)vinyl]-5-methyl-4-piperidinopyridine
(103) (Z)-2-[2-(4-biphenylyl)vinyl]-5-methyl-4-(perhydroazepin-1-yl)pyridine
(104) (E)-5-methyl-2-(2-phenylvinyl)-4-piperidinopyridine
(105) (Z)-5-methyl-2-(2-phenylvinyl)-4-piperidinopyridine
(106) (E)-5-methyl-2-[2-(2-naphthyl)vinyl]-4-piperidinopyridine
(107) (Z)-5-methyl-2-[2-(2-naphthyl)vinyl]-4-piperidinopyridine
(108) (E)-5-methyl-2-[2-(6-methyl-2-naphthyl)-vinyl]-4-piperidinopyridine
(109) (Z)-5-methyl-2-[2-(6-methyl-2-naphthyl)-vinyl]-4-piperidinopyridine
(110) (E)-5-methyl-2-[2-methyl-2-(2-naphthyl)-vinyl]-4-piperidinopyridine
(111) (E)-2-[2-(4-biphenylyl)vinyl]-4-methoxy-5-methylpyridine
(112) (E)-4-benzyloxy-5-methyl-2-(2-phenylvinyl)-pyridine
(113) (Z)-4-benzyloxy-5-methyl-2-(2-phenylvinyl)-pyridine
(114) (Z)-2-[2-(2-chlorophenyl)vinyl]-5-methyl-4-piperidinopyridine
(115) (E)-2-[2-(2,3-dichlorophenyl)vinyl]-5-methyl-4-piperidinopyridine
(116) (Z)-2-[2-(2,3-dichlorophenyl)vinyl]-5-methyl-4-piperidinopyridine
(117) (Z)-2-[2-(2,3-dimethylphenyl)vinyl]-5-methyl-4-piperidinopyridine
(118) (E)-2-[2-(2-ethoxycarbonylphenyl)vinyl]-5-methyl-4-piperidinopyridine
(119) (Z)-2-[2-(2-ethoxycarbonylphenyl)vinyl]-5-methyl-4-piperidinopyridine
(120) 5-methyl-4-(4-methylpiperidino)-2-[2-(1-naphthyl)ethyl]pyridine
(121) 5-methyl-2-[2-(1-naphthyl)ethyl]-4-piperidinopyridine
(122) 2-[2-(2-methoxy-1-naphthyl)ethyl]-5-methyl-4-piperidinopyridine
(123) 5-methyl-2-[(4-methyl-1-naphthyl)-ethyl]-4-piperidinopyridine
(124) 2-[2-(4-methoxy-1-naphthyl)ethyl]-5-methyl-4-piperidinopyridine
(125) 5-methyl-2-[2-(5-methyl-1-naphthyl)-ethyl]-4-piperidinopyridine
(126) 5-methyl-2-[2-(5-methoxy-1-naphthyl)-ethyl]-4-piperidinopyridine
(127) 5-methyl-2-[2-(7-methoxy-1-naphthyl)-ethyl]-4-piperidinopyridine
(128) 5-methyl-2-[2-(8-methyl-1-naphthyl)-ethyl]-4-piperidinopyridine
(129) 5-methyl-2-[2-(8-methyl-1-naphthyl)-ethyl]-4-(perhydroazepin-1-yl)pyridine
(130) 5-methyl-2-[2-(1-naphthyl)ethyl]pyridine
(131) 4-methoxy-5-methyl-2-[2-(1-naphthyl)-ethyl]-4-piperidinopyridine
(132) 5-methyl-2-[2-(1-naphthyl)ethyl]-4-propoxypyridine
(133) 4-isopentyloxy-5-methyl-2-[2-(1-naphthyl)ethyl]pyridine
(134) 4-hexyloxy-5-methyl-2-[2-(1-naphthyl)-ethyl]-pyridine
(135) 5-methyl-2-[2-(1-naphthyl)ethyl]-4-pentyloxypyridine
(136) 4-cyclohexyloxy-2-[2-(1-naphthyl)ethyl]-pyridine
(137) 4-cyclohexyloxy-5-methyl-2-[2-(1-naphthyl)ethyl]pyridine
(138) 4-cyclohexyloxy-5-ethyl-2-[2-(1-naphthyl)ethyl]pyridine
(139) 5-methyl-2-[2-(1-naphthyl)ethyl]-4-phenoxypyridine
(140) 5-methyl-2-[2-(1-naphthyl)ethyl]-4-phenethyloxypyridine
(141) 4-dimethylamino-5-methyl-2-[2-(1-naphthyl)ethyl]pyridine
(142) 5-methyl-4-(pyrrolidin-1-yl)-2-[2-(1-naphthyl)ethyl]pyridine
(143) 5-methyl-4-morpholino-2-[2-(1-naphthyl)-ethyl]pyridine
(144) 5-methyl-4-(4-methylpiperazin-1-yl)-2-[2-(1-naphthyl)ethyl]pyridine
(145) 5-methyl-2-[2-(1-naphthyl)ethyl]-4-(perhydroazepin-1-yl)pyridine
(146) 5-ethyl-2-[2-(1-naphthyl)ethyl]-4-(1-perhydroazepin-1-yl)pyridine
(147) 5-methyl-4-(3-methylpiperidino)-2-[2-(1-naphthyl)ethyl]pyridine
(148) 4-diethylamino-5-methyl-2-[2-(1-naphthyl)ethyl]pyridine
(149) 5-methyl-2-[2-(1-naphthyl)ethyl]-4-piperidinopyridine
(150) 5-ethyl-2-[2-(1-naphthyl)ethyl]-4-piperidinopyridine
(151) 2-[2-(1-naphthyl)ethyl]-4-piperidino-5-propylpyridine
(152) 3-[2-(1-naphthyl)ethyl]-2-piperidinopyridine
(153) 4-[2-(1-naphthyl)ethyl]-2-piperidinopyridine
(154) 6-methyl-2-[2-(1-naphthyl)ethyl]-4-piperidinopyridine
(155) 3-[2-(2-naphthyl)ethyl]-4-piperidinopyridine
(156) 2-[2-(2-naphthyl)ethyl]-6-piperidinopyridine
(157) 2-[2-(4-biphenylyl)ethyl]-5-methyl-4-piperidinopyridine
(158) 5-methyl-2-phenethyl-4-piperidinopyridine
(159) 5-methyl-2-[2-(6-methyl-2-naphthyl)-ethyl]-4-piperidinopyrine
(160) 5-methyl-2-[2-methyl-2-(2-naphthyl)-ethyl]-4-piperidinopyridine
(161) 5-methyl-2-[2-(2-naphthyl)ethyl]-4-piperidinopyridine
(162) 2-[2-(4-biphenylyl)ethyl]-4-methoxy-5-methylpyridine
(163) 2-[2-(2-ethoxycarbonylphenyl)ethyl]-5-methyl-4-piperidinopyridine
(164) 2-[2-(4-fluoro-2-naphthyl)ethyl]-5-methyl-4-piperidinopyridine (165) 2-[2-(4-chloro-2-naphthyl)ethyl]-5-methyl-4-piperidinopyridine (166) 2-[2-(2-chlorophenyl)ethyl]-5-methyl-4-piperidinopyridine (167) 2-[2-(2,3-dichlorophenylethyl]-5-methyl-4-piperidinopyridine (168) 4-benzyloxy-5-methyl-2-[2-(1-naphthyl)-ethyl]-pyridine.

Preferred among the above exemplified compounds are compounds Nos. 20, 23, 26, 27, 29, 30, 32, 34, 36, 40, 41, 54, 74, 75, 77, 78, 80, 81, 87, 88, 90, 116, 117, 120, 121, 123, 124, 125, 126, 128, 137, 145, 146, 147, 163, 164, and 165. Most preferred are compounds Nos. 20, 23, 26, 29, 32, 34, 36, 40, 54, 74, 77, 80, 87, 116, 117, 120, 121, 123, 124, 125, 126, 128, 137, 145, 147, 163, 164 and 165.

The compounds of this invention are basic and can form acid addition salts with inorganic or organic acids. Examples of the acids that can form such acid addition salts include inorganic acids such as hydrochloric acid, sulfuric acid, hydrobromic acid, phosphoric acid and nitric acid; organic acids such as formic acid, acetic acid, propionic acid, succinic acid, glycolic acid, lactic acid, malic acid, tartaric acid, citric acid, maleic acid, phenylacetic acid, benzoic acid, salicylic acid, methanesulfonic acid, toluenesulfonic acid and benzenesulfonic acid; amino acids such as aspartic acid and glutamic acid. Preferred acid addition salts are pharmaceutically acceptable acid addition salts.

The compounds of this invention can be produced by various methods according to the type of the substituents. These methods will be described below.

(a) Compounds of formula [Ic]]corresponding to formula [I] wherein m and n are 1, X represents an oxygen atom, a sulfur atom or a group of the formula -N-R$^a$ in which R$^a$ is a hydrogen atom or a lower alkyl group, and Y is a linear or branched lower alkylene group may be produced by a method shown by the following reaction scheme 1.

Reaction scheme 1

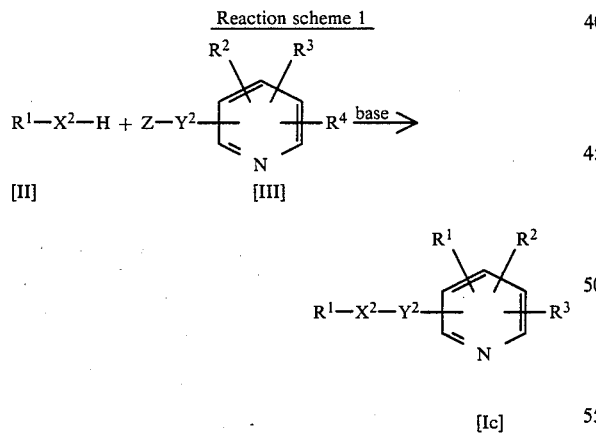

In the above formulae, X$^2$ represents an oxygen atom, a sulfur atom, or a group of the formula -N-R$^a$ in which R$^a$ is a hydrogen atom or a lower alkyl group; Y$^2$ represents a linear or branched lower alkyl group; Z represents a halogen atom such as a chlorine, bromine or iodine atom, an alkylsulfonyloxy group such as a methanesulfonyloxy, ethanesulfonyloxy or propanesulfonyloxy group, or an aromatic sulfonyloxy group such as a benzenesufonyloxy or p-toluenesulfonyloxy group; and R$^1$, R$^2$, R$^3$ and R$^4$ are as defined hereinabove.

The condensation reaction between the compound of formula [II] and the compound of formula [III] or its acid addition salt is usually carried out in a suitable solvent in the presence of a base. Examples of the solvent that can be used in the reaction are alcohols such as methanol, ethanol and propanol, ethers such as tetrahydrofuran, dioxane, diethyl ether and diisopropyl ether, dimethylformamide, dimethyl sulfoxide and mixtures of these with water. Examples of the base are alkali metal hydroxides such as sodium hydroxide, potassium hydroxide and lithium hydroxide, alkali metal hydrides such as sodium hydride and potassium hydride, alkali metal carbonates such as sodium carbonate, sodium hydrogen carbonate and potassium hydrogen carbonate, and organic amines such as triethylamine and pyridine. The reaction is carried out usually at 0° C. to the boiling point of the solvent, preferably 25° C. to the refluxing temperature.

The proportion of the compound of formula (II) relative to the compound of formula (III) is not critical, and can be varied over a wide range depending upon the type of the compound of formula (II) and/or (III). Generally, the compound of formula (II) is used in an amount of 0.5 to 2 moles, preferably 0.8 to 1.2 moles, per mole of the compound of formula (III). Preferably, the base is used in an amount of 1 to 3 moles per mole of the compound of formula (III).

After the reaction, the resulting compound of formula [Ic] is isolated from the reaction mixture and purified by separating means known per se, such as solvent extraction, recrystallization, and chromatography.

(b) Compounds of the following formula [Id] corresponding to general formula [I] in which m is 0, n is 1, and Y is a vinylene group which may optionally be substituted by a lower alkyl group may be produced by a method shown by the following reaction scheme 2.

Reaction scheme 2

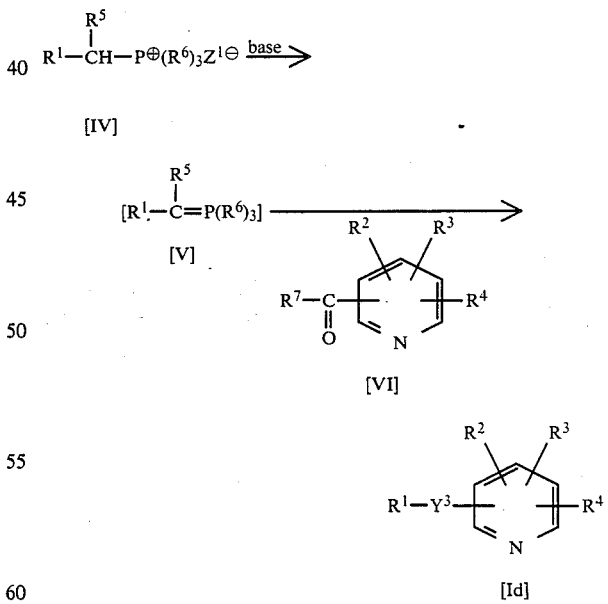

In the formulae, R$^5$ represents a hydrogen atom or a lower alkyl group; R$^6$ represents an aryl group such as a phenyl group or a lower alkyl group such as a methyl, ethyl, propyl, butyl or pentyl group; Y$^3$ represents a vinylene group which may optionally be substituted by a lower alkyl group; Z$^1$ represents a halogen atom such as a chlorine, bromine or iodine atom; R$^7$ represents a hydrogen atom or a lower alkyl group; and $R^1$, $R^2$, $R^3$ and $R^4$ are as defined hereinabove.

Conversion of the phosphonium salt of general formula [IV] into the phospholan of formula [V] is carried out usually in a suitable solvent in the presence of a base. Examples of the solvent that can be used in this reaction are ethers such as diethyl ether, diisopropyl ether, tetrahydrofuran, dioxane and 1,2-dimethoxyethane; aromatic solvents such as benzene, toluene and xylene; and aprotic polar solvents such as dimethylformamide, dimethylacetamide and dimethyl sulfoxide. The base may be any of those which are used in the ordinary Wittig reaction. Suitable bases include, for example, organic lithium compounds such as methyllithium, butyllithium, sec-butyllithium, phenyllithium, lithiumdiethylamide and lithiumdiisopropylamide, alkali metal hydrides such as sodium hydride and potassium hydride, alkali metal alcoholates such as sodium methoxide and potassium tert-butoxide, and alkali metal amides such as sodium amide and potassium amide.

The above bases and solvents are desirably used in combination according to the properties of both.

The conversion of the phosphonium salt of formula [IV] into the phospholan of formula [V] readily proceeds at $-50°$ to $-10°$ C. by the addition of the base, and then, by adding the aldehyde or ketone compound of formula [VI], the reaction can be continued.

The amount of the base used in the above conversion may generally be 0.8 to 1.5 moles per mole of the compound of formula [IV].

The reaction temperature in the two-stage reaction differs depending upon the reactivity between the aldehyde or ketone compound of formula [VI] and the phospholan compound of formula [V], but is usually from $-50°$ C. to the boiling point of the solvent, preferably from $-30°$ C. to the refluxing temperature. Preferably, the above reaction is carried out in a stream of an inert gas such as helium, nitrogen or argon. The reaction usually ends in 0.5 to 10 hours.

The amount of the compound of formula [VI] used is not critical. Generally, its amount is conveniently 0.5 to 2 moles, preferably 0.8 to 1.2 moles, per mole of the phosphonium salt of formula [IV]. The reaction product of formula [Id] is usually obtained as a mixture of E- and Z-isomers. As required, after the reaction, these isomers may be isolated and purified by known techniques such as column chromatography and recrystallization.

(c) Compounds of formula [I] in which m is 0, n is 1, and Y is an ethylene group which may optionally be substituted by a lower alkyl group may be obtained by reducing the vinylene compound represented by general formula [Id] obtained by the above method. The vinylene compound may be an E-isomer, or a Z-isomer, or a mixture of both. The reducing reaction can be easily performed by a method known per se, for example by catalytic reduction using a catalyst such as Raney nickel, platinum, or palladium-carbon. The reducing reaction can be carried out within several hours at room temperature to an elevated temperature using a solvent, for example an alcohol such as methanol or ethanol, an ether such as tetrahydrofuran or dioxane, if required under an elevated pressure. After the reaction, the desired ethylene compound can be obtained by isolation and purification by known methods.

(d) Compounds of formula [Ie] corresponding to general formula [I] in which m is 1, n is 0, and X is $$\begin{array}{c} \text{OH} \\ | \\ -\text{CH}- \end{array},$$

compounds of formua [If] corresponding to formula [I] in which m is 1, n is 0 and X is a carbonyl group, and compounds of formula [Ig] corresponding to general formula [I] in which m is 0, n is 1 and Y is a methylene group may be produced by a method shown in the following reaction scheme 3.

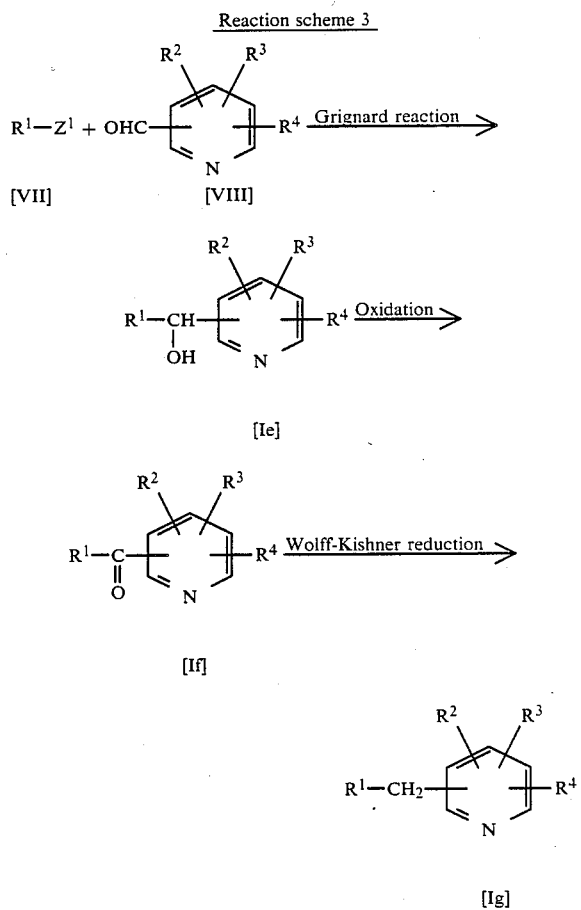

In the formulae, $R^1$, $R^2$, $R^3$, $R^4$ and $Z^1$ are as defined hereinabove.

The Grignard reaction between the aromatic halogen compound of general formula [VII] and the aldehyde compound of general formula [VIII] may be carried out by a method known per se. The resulting carbinol compound of formula [Ie] may be easily converted to the corresponding ketone compound of formula [If] by oxidizing it with an oxidizing agent such as manganese dioxide, potassium permanganate, or potassium bichromate. The ketone compound is heated with hydrazine hydrate at 130° to 240° C. for 1 to 4 hours in the presence of a base such as potassium hydroxide (Wolff-Kishner reduction) to give the methylene compound of formula [Ig].

(e) Compounds of formulae [Ih] to [Ij] corresponding to general formula [I] in which m and n are 1, X is a carbonyl group or a group of the formula $$\begin{array}{c} \text{OH} \\ | \\ -\text{CH}- \end{array}$$

and Y is an ethylene or vinylene group, and compounds of formula [Ik] corresponding to general formula [I] in which m is 0, n is 1 and Y is a trimethylene group can be produced in accordance with the following reaction scheme 4.

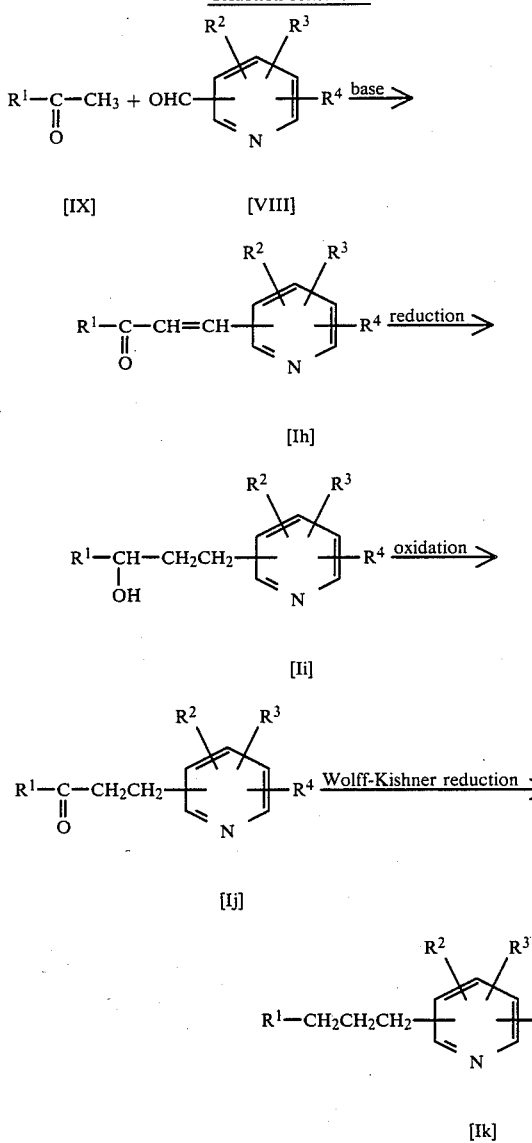

In the above formulae, $R^1$, $R^2$, $R^3$ and $R^4$ are as defined above.

The condensation reaction between the ketone compound of general formula [IX] and the pyridinealdehyde compound of general formula [VIII] is carried out in water or a hydrous alcohol in the presence of a basic catalyst such as sodium hydroxide or potassium hydroxide. Usually, the reaction temperature is 0° to 30° C., and the reaction time is 1 to 24 hours.

The proportion of the compound of formula [IX] relative to the compound of formula [VIII] is not strictly limited, and can be varied over a wide range. Generally, the compound of formula [IX] is used in a proportion of 0.5 to 2 moles, preferably 0.8 to 1.5 moles, per mole of the compound of formula [VIII]. The resulting alpha,beta-unsaturated ketone compound [Ih] is reacted with lithium aluminum hydride at room temperature or at an elevated temperature in a manner known per se to yield the alcohol compound of formula [Ii]. This reducing reaction is carried out in an inert solvent such as diethyl ether or tetrahydrofuran, usually using 1 to 2 equivalents of lithium aluminum hydride per mole of the compound of formula [Ih].

Then, the resulting alcohol compound [Ii] is reacted with an oxidizing agent such as manganese dioxide, potassium permanganate or potassium bichromate, preferably manganese dioxide in methylene chloride or chloroform, at room temperature to the boiling point of the solvent to give the ketone compound [Ij]. Wolff-Kishner reaction of the ketone compound [Ij] gives the trimethylene compound [Ik].

The starting materials and the reaction intermediates used in the production of the compound of this invention are produced by the following methods.

The aromatic compound of general formula [II] having a hydroxyl, amino or mercapto group on the ring which is used to synthesize the compound of formula [Ic] is commercially available, or may be produced by known techniques.

Of the substituted pyridinehalomethyl compounds and alkyl or arylsulfonyloxymethyl compounds of general formula [III] as the other starting material, those in which $Z$-$Y^2$ is substituted at the 2- or 4-position of the pyridine ring (i.e., compounds of formula [IIIa]) can be produced by a method shown in the following reaction scheme 5.

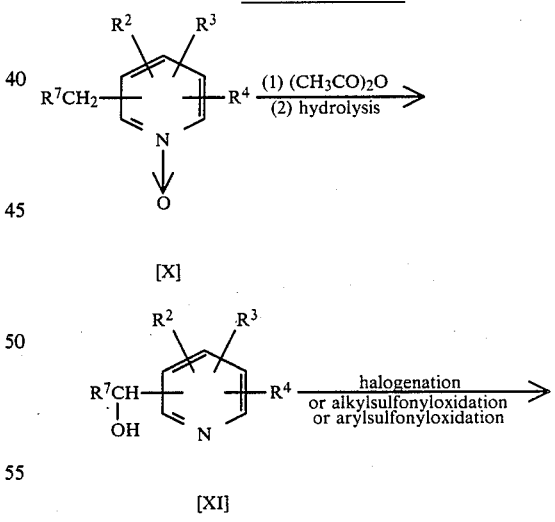

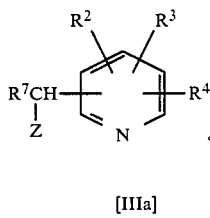

In the formulae, $R^1$, $R^2$, $R^3$, $R^4$, $R^7$ and Z are as defined hereinabove.

An N-oxide compound of general formula [X] is heated under reflux with acetic anhydride for 1 to 4 hours to perform rearrangement reaction. The product is then subjected to ordinary acid or alkaline hydrolysis, alcoholysis or ammonolysis to give an alcohol compound of formula [XI]. The starting material of formula [X] can be produced by methods similar to those described in J. Med. Chem., vol. 19, page 1029 (1976) and Japanese Laid-Open Patent Publication Nos. 59662/1984 and 109788/1986. The substituted pyridinemethanol of formula [XI] can be converted to the halomethyl compound or alkyl- or arylsulfonyloxymethyl compound of formula [III] by reacting with thionyl chloride, phosphorus tribromide, hydrobromic acid, etc., preferably with thionyl chloride in methylene chloride or chloroform, at 0° C. to room temperature to halogenate it, or sulfonyloxidizing it with an alkylsulfonyl chloride or an arylsulfonyl chloride.

Of the compounds of general formula [III], those in which $Z-Y^2-$ is substituted at the 3-position of the pyridine ring (i.e., compounds of formula [IIIb]) can be produced, for example, by a method of the following reaction scheme 6.

Reaction scheme 6

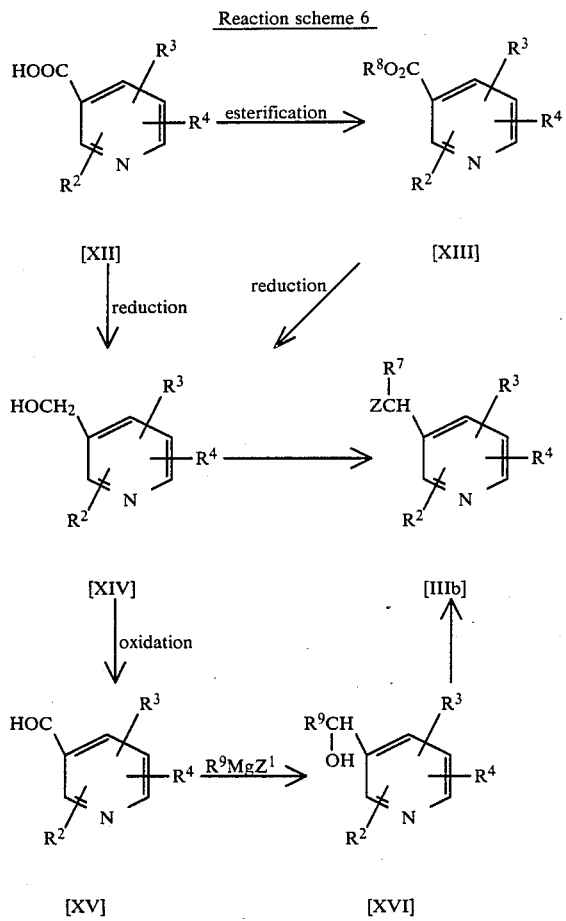

In the above formulae, $R^8$ and $R^9$ represent a lower alkyl group, and $R^2$, $R^3$, $R^4$, $R^7$, Z and $Z^1$ are as defined hereinabove.

A substituted pyridine-3-methanol represented by general formula [XIV] can be produced by reducing a substituted pyridine-3-carboxylic acid of formula [XII] with lithium aluminum hydride to an alcohol compound of formula [XIV] or esterifying it with an ethanol solution of hydrogen chloride or an ethanol solution of thionyl chloride to form a compound of formula [XIII], and reducing it with lithium aluminum hydride, sodium borohydride or sodium borohydride-calcium chloride to reduce it to the alcohol. Oxidation of the compound of formula [XIV] with manganese dioxide, chromium trioxide-pyridine, etc. gives the corresponding aldehyde compound of formula [IV]. The compound [XVI] may be obtained by reacting the compound of formula [XV] at 0° C. to room temperature in a solvent such as ethyl ether or tetrahydrofuran with a Grignard reagent prepared from an alkyl chloride or bromide and magnesium. Halogenation or alkyl- or arylsulfonyloxidation of the substituted pyridine-3-carbinol of general formula [XIV] or [XVI] gives a 3-haloalkyl or 3-alkyl, or 3-arylsulfonyloxyalkylpyridine compound of formula [IIIb]. The starting material of formula [XII] can be produced by a series of methods described in J. Org. Chem., vol. 19, page 1633 (1954), J. Org. Chem., vol. 38, page 3268 (1973), Chemical Abstracts, vol. 67, 64196j, and J. Am. Chem. Soc., vol. 76, page 1286 (1954).

The phosphonium salt of general formula [IV] used to produce the compound of general formula [Id] can be obtained by heating a benzene, biphenylyl or naphthalene derivative having a halomethyl group on the ring represented by the general formula

[XVII]

wherein $R^1$, $R^6$ and $Z^1$ are as defined hereinabove, under reflux together with a phosphine compound of the general formula $$P(R^6)_3 \qquad [XVIII]$$

wherein $R^6$ is as defined hereinabove, usually in a solvent such as benzene. The halomethyl compound [XVII] is commercially available, or may be produced by, for example, reacting an alkyl-substituted aromatic compound with N-bromosuccinimide in a solvent such as carbon tetrachloride under heat to halogenate the alkyl group, or by reacting an aromatic carboxylic acid, ester, ketone or aldehyde with, for example, lithium aluminum hydride or sodium borohydride in ethyl ether or tetrahydrofuran usually at 0° C. to the boiling point of the solvent to form an alcohol compound and then halogenating the hydroxyl group of the alcohol compound with thionyl chloride, phosphorus tribromide, hydrobromic acid, etc.

The substituted pyridinealdehyde or ketone compound, the other starting material used to produce the compound of general formula [Id] may be produced by oxidizing the substituted pyridinecarbinol compound of general formula [XI], [XIV] or [XVI] using manganese dioxide, chromium trioxide-pyridine, potassium permanganate or selenium dioxide, preferably manganese dioxide, in methylene chloride or chloroform at room temperature or at an elevated temperature.

The compounds of formula [I] provided by this invention are characteristic in that they have excellent pharmacological properties, particularly excellent gastric acid antisecretory activity and gastric mucosa protecting activity.

These pharmacological properties of the compounds of this invention are demonstrated by the following pharmacological test example.

PHARMACOLOGICAL TEST EXAMPLE

Test compounds were as follows:

(1) 5-methyl-2-phenoxymethyl-4-piperidinopyridine hydrochloride (Example 3)

(2) 2-[(4-tert-butylphenoxy)methyl]-5-methyl-4-piperidinopyridine (Example 4)

(3) 2-[(4-sec-butylphenoxy)methyl]-5-methyl-4-piperidinopyridine hydrochloride (Example 5)

(4) 2-[(4-cyclohexylphenoxy)methyl]-5-methyl-4-piperidinopyridine (Example 7)

(5) 5-methyl-2-phenylthiomethyl-4-piperidinopyridine hydrochloride (Example 12)

(6) 5-methyl-2-[(2-naphthyl)thiomethyl]-4-piperidinopyridine hydrochloride (Example 13)

(7) (Z)-5-methyl-2-[2-(1-naphthyl)vinyl]-4-piperidinopyridine hydrochloride (Example 14-B)

(8) (Z)-2-[2-(4-chloro-1-naphthyl)vinyl]-5-methyl-4-piperidinopyridine hydrochloride (Example 17-B)

(9) (Z)-2-[2-(4-fluoro-1-naphthyl)vinyl]-5-methyl-4-piperidinopyridine hydrochloride (Example 18-B)

(10) (Z)-2-[2-(5-methyl-1-naphthyl)vinyl]-5-methyl-4-piperidinopyridine hydrochloride (Example 20-B)

(11) (Z)-2-[2-(8-methyl-1-naphthyl)vinyl]-5-methyl-4-piperidinopyridine (Example 22-B)

(12) (Z)-4-cyclohexyloxy-5-methyl-2-[2-(1-naphthyl)-vinyl]pyridine (Example 28-B)

(13) (Z)-5-methyl-2-[2-(1-naphthyl)vinyl]-4-(perhydroazepin-1-yl)pyridine hydrochloride (Example 37-B)

(14) (Z)-5-methyl-4-(4-methylpiperidino)-2-[2-(1-naphthyl)vinyl]pyridine hydrochloride (Example 38-B)

(15) (Z)-5-methyl-4-(3-methylpiperidino)-2-[2-(1-naphthyl)vinyl]pyridine hydrochloride (Example 39-B)

(16) (Z)-3-[2-(2-naphthyl)vinyl]-4-piperidinopyridine (Example 47-B)

(17) (E)-5-methyl-2-[2-(2-naphthyl)vinyl]-4-piperidinopyridine hydrochloride (Example 51-A)

(18) (Z)-5-methyl-2-[2-(2-naphthyl)vinyl]-4-piperidinopyridine hydrochloride (Example 51-B)

(19) (Z)-5-methyl-2-[2-(6-methyl-2-naphthyl)-vinyl]-4-piperidinopyridine (Example 52-B)

(20) (Z)-2-[2-(2,3-dichlorophenyl)vinyl]-5-methyl-4-piperidinopyridine hydrochloride (Example 57-B)

(21) 5-methyl-4-(4-methylpiperidino)-2-[2-(1-naphthyl)ethyl]pyridine (Example 62)

(22) 5-methyl-2-[2-(1-naphthyl)ethy]-4-piperidinopyridine hydrochloride (Example 63)

(23) 5-methyl-2-[2-(4-methyl-1-naphthyl)-ethyl]-4-piperidinopyridine hydrochloride (Example 65)

(24) 5-methyl-2-[2-(8-methyl-1-naphthyl)-ethyl]-4-piperidinopyridine hydrochloride (Example 70)

(25) 4-cyclohexyloxy-5-methyl-2-[2-(1-naphthyl)ethyl]pyridine hydrochloride (Example 76)

(26) 5-methyl-4-(3-methylpiperidino)-2-[2-(1-naphthyl)ethyl]pyridine hydrochloride (Example 84)

(27) 5-methyl-2-phenethyl-4-piperidinopyridine hydrochloride (Example 95)

(28) 5-methyl-2-[2-(2-naphthyl)ethyl]-4-piperidinopyridine hydrochloride (Example 96)

(29) 5-methyl-2-[2-(6-methyl-2-naphthyl)-ethyl]-4-piperidinopyridine hydrochloride (Example 97)

Testing methods (1) Inhibitory effects on the activity of $H^+,K^+$-ATPase

Rabbit gastric glands were homogenized and microsomal fractions were prepared by differential centrifugation of the resultant homogenate. The microsomal fractions were layered on 37% sucrose and centrifuged to obtain light membrane fractions containing $H^+,K^+$-ATPase. Using the $H^+,K^+$-ATPase-containing fractions, the effects of the compounds of this invention and omeprazole on the activity of $H^+,K^+$-ATPase were examined. The inhibitory activities of the compounds of this invention on $H^+,K^+$-ATPase measured by the above method are shown in Table I.

TABLE 1

| Test compound No. | 50% Enzyme inhibitory concentration ($IC_{50}$, M) |
| --- | --- |
| 1 | $8.4 \times 10^{-6}$ |
| 2 | $3.5 \times 10^{-6}$ |
| 3 | $4.1 \times 10^{-6}$ |
| 4 | $3.8 \times 10^{-6}$ |
| 5 | $1.6 \times 10^{-5}$ |
| 6 | $9.0 \times 10^{-6}$ |
| 7 | $2.2 \times 10^{-6}$ |
| 8 | $4.8 \times 10^{-6}$ |
| 9 | $5.9 \times 10^{-6}$ |
| 10 | $6.0 \times 10^{-6}$ |
| 11 | $2.3 \times 10^{-6}$ |
| 12 | $3.5 \times 10^{-6}$ |
| 13 | $7.8 \times 10^{-7}$ |
| 14 | $2.8 \times 10^{-6}$ |
| 15 | $1.7 \times 10^{-6}$ |
| 16 | $2.6 \times 10^{-6}$ |
| 17 | $4.3 \times 10^{-6}$ |
| 18 | $8.4 \times 10^{-6}$ |
| 19 | $7.8 \times 10^{-6}$ |
| 20 | $4.6 \times 10^{-6}$ |
| 21 | $2.7 \times 10^{-6}$ |
| 22 | $3.6 \times 10^{-6}$ |
| 23 | $4.6 \times 10^{-6}$ |
| 24 | $6.0 \times 10^{-6}$ |
| 25 | $2.6 \times 10^{-6}$ |
| 26 | $1.7 \times 10^{-6}$ |
| 28 | $3.0 \times 10^{-6}$ |
| 29 | $2.3 \times 10^{-6}$ |
| omeprazole (control) | $6.2 \times 10^{-6}$ |

The above test results clearly show that the compounds of this invention have strong inhibitory activity on $H^+,K^+$-ATPase, and excellent as a gastric acid antisecretory agent and thus an antiulcer agent.

(2) Gastric acid antisecretory activity

The method of preparation was based on the technique of Osumi et al. (see "Life Science" 20, 1407, 1977).

Male Doryu rats weighing about 250 g were deprived of food for 24 hours but were allowed free access to water before experiments.

Under urethane anesthesia (1.25 g/kg i.p.), the femoral vein was cannulated for infusion of histamine (2 mg/kg/hr), and the juglar vein was cannulated for the administration of test compounds. The esophagus was ligated, and bilateral vagus nerves were carefully separated and cut at the cervical portion. The abdomen was opened by a midoline incinion, and a polyethylene cannula (about 3.5 cm in length and 0.4 cm in diameter) was inserted into the stomach via an incision in the duodenum.

After washout of the stomach with saline, 2.0 ml of fresh saline prewarmed at 38° C. was instilled and replaced with fresh solution at 15 min intervals.

Several successive collections of basal acid secretion were made to confirm the steady level of secretion. After these collections, gastric acid secretion was enhanced by infusion of histamine. Gastric acid secretion was determined as follows: the total value of gastric solution recovered from the stomach every 15 min was titrated to pH 7.0 with 0.1N NaOH, using an automatic titrator (Radiometer, Copenhage, Denmark). Acid output secreted for 15 min were calculated as microequivalents per 15 min.

75 min after the starting of infusion, each test compound dissolved in methanol or only methanol (control) was administered through the jugular vein at doses of 0.3, 1.0 and 3.0 mg/kg of 3.0, 10.0 and 30.0 mg/kg. From the acid output in a control group measured at the time when the acid output secreted was lowest, the acid secretion inhibitory ratio (R) was calculated in accordance with the following equation.

$$R = \frac{V^o - V}{V^o} \times 100(\%)$$

wherein $V^o$ is the acid output produced when the animals were not treated with the test compounds (control), and V is the acid output acid produced when the test compounds were administered to the animals.

Furthermore, from correlation line between the dose and the inhibitory ratio at the dose by using the method of least squares, the 50% inhibitory dose was determined. The results are shown in Table II.

TABLE II

| Gastric acid antisecretory activity | |
|---|---|
| Test compound No. | 50% Effective dose ($ED_{50}$, mg/kg) |
| 7 | 1.16 |
| 8 | 2.78 |
| 11 | 0.92 |
| 12 | 1.35 |
| 13 | 0.90 |
| 14 | 1.09 |
| 15 | 0.99 |
| 21 | 0.78 |
| 22 | 2.50 |
| 24 | 2.72 |
| 25 | 0.91 |
| 26 | 0.91 |

The above test results clearly show that the compounds of this invention have marked gastric acid antisecretory activity and are promising as an antiulcer agent.

(3) Effect of preventing gastric ulcer induced by ethanol-hydrochloric acid

According to the method of Robert et al. (see "Gastroenterology" 77, 433–443 (1979), SD-strain rats (male, weighing 200 to 220 g, 8 rats in each group) were deprived of food for 24 hours and of water for 19 hours. Each of the test compounds was suspended in 0.5% carboxymethyl cellulose, and orally administered to the rats. Thirty minutes after administration, 0.2N hydrochloric acid-50% ethanol (1 ml/rat) was orally administered. One hour after the administration of ethanol-hydrochloric acid, the rats were killed. The stomachs were dissected out, and the lower part of the esophagus was nipped with a clip. Aqueous 1% formalin solution (12.0 ml) was poured into the stomachs from the duodenum and then the duodenum part was nipped with a clip. The whole stomachs were immersed in aqueous 1% formalin for about 10 minutes for fixation. The stomachs were opened along the greater curvature and then rinsed with water. The gastric mucosa was examined and the lengths of bleeding erosions which occurred in the glandular stomach were measured in mm under an anatomic microscope. From the test results obtained by the above method, the $ED_{50}$ (50% effective dose) of each of the test compounds was calculated. The results are shown in Table III.

TABLE III

| Test compound No. | 50% Effective dose ($ED_{50}$, mg/kg) |
|---|---|
| 1 | 12.1 |
| 5 | 9.2 |
| 6 | 7.3 |
| 22 | 5.4 |
| 27 | 5.4 |
| 28 | 3.6 |
| omeprazole (control) | 34.1 |

The above test results clearly show that the compounds of this invention have marked inhibitory activity on ulcer induced by ethanol-hyrochloric acid as compared with omeprazole.

It is clear from the above pharmacological test results that the compounds of this invention show strong gastric acid antisecretory activity and gastrointestinal cell protecting activity, and are useful as antiulcer agents.

The compound of this invention can be administered in a therapeutically effective amount as an antiulcer agent to man and other mammals for the treatment or therapy of ulcer either orally or parenterally (e.g., intramuscularly, intravenously, subcutaneously, intrarectally, intradermally), preferably orally. For use as the antiulcer agent, the compound of this invention can be prepared into forms suitable for oral or parenteral administration together with pharmaceutically acceptable adjuvants. The compound of this invention can be formulated by using additives normally used in drugs, for example vehicles, binders, lubricants, disintegrants, antiseptics, isotonic agents, stabilizers, dispersing agents, antioxidants, coloring agents, flavoring agents and buffers. The pharmaceutical preparations may be in various dosage forms according to their use, for example in a solid form (such as tablets, hard capsules, soft capsules, granules, powders, pellets, pills and trouches), a semisolid form (such as suppositories and ointments) and a liquid form (such as injectable preparations, emulsions, suspensions and syrups).

Nontoxic additives which can be used include lactose, fructose, glucose, starch, gelatin, magnesium carbonate, magnesium meta-silicate aluminate, synthetic aluminum silicate, silicic anhydride, talc, magnesium stearate, methyl cellulose, carboxymethyl cellulose or its salts, gum arabic, polyethylene glycol, alkyl p-hydroxybenzoates, syrup, ethanol, propylene glycol, Vaseline, carbowax, glycerol, sodium chloride, sodium sulfate, sodium phosphate and citric acid. The pharmaceutical preparation comprises the compound of this invention in a therapeutically effective amount. The concentration of the compound of this invention varies according to the form of the pharmaceutical preparation. Generally, it is 5 to 100% by weight for solid and semisolid forms and 0.1 to 10% by weight for a liquid form. The dose of the compound of this invention can be varied depending upon the type of the human or other mammalian subject, the route of administration, the severity of the condition, etc. Usually, it may be 0.01 to 20 mg/kg per day. It may, however, be increased or decreased by the conditions of the subject or the physician's judgment.

The above dose may be administered once or in several divided doses per day.

The following Examples illustrate the production of the compounds of this invention.

EXAMPLE 1

Production of 5-methyl-2-[(1-naphthyl)oxymethyl]-4-piperidinopyridine:

A 10% aqueous solution of sodium hydroxide (0.40 ml; 1.00 mmole) was added to a solution of 144 mg (1.00 mmole) of alpha-naphtol and 106 mg (0.41 mmole) of 2-chloromethyl-5-methyl-4-piperidinopyridine hydrochloride in 5 ml of ethanol, and the mixture was heated under reflux for 3 hours. The solvent was evaporated under reduced pressure. After adding a saturated aqueous sodium chloride solution to the residue, the mixture was extracted with chloroform. The chloroform layer was dried over anhydrous magnesium sulfate and concentrated under reduced pressure. The residue was purified by silica gel column chromatography [eluted with n-hexane/acetone (10/1)] to give 108 mg (yield 80%) of the captioned compound as crystals.

m.p. 101°–102° C.

IR(KBr, cm$^{-1}$): 3060, 3015, 2930, 2805, 1595, 1585, 1410, 1385, 1240, 1110, 795.

NMR(CDCl$_3$, δ ppm): 1.62(6H, br s), 2.21(3H, s), 2.80–3.10(4H, m), 5.27(2H, s), 6.86(1H, dd, J=2,6 Hz), 7.10(1H, s), 7.10–7.90(5H, m), 8.21(1H, s), 8.20–8.40(1H, m).

EXAMPLES 2–9

In the same way as in Example 1, the following compounds of Examples 2 to 9 were prepared.

EXAMPLE 2

5-Methyl-2-[(2-naphthyl)oxymethyl]-4-piperidinopyridine m.p. 187°–190° C.

IR(KBr, cm$^{-1}$): 3440, 3040, 2930, 2850, 1640, 1605, 1455, 1385, 1185, 860.

NMR((CD$_3$)$_2$SO, δ ppm): 1.66(6H, br s), 2.31(3H, s), 3.44(4H, br s), 5.45(2H, s), 7.10–8.00(8H, m), 8.24(1H, s).

EXAMPLE 3

5-methyl-2-phenoxymethyl-4-piperidinopyridine hydrochloride m.p. 148°–149° C.

IR(KBr, cm$^{-1}$): 3360, 2930, 2850, 1640, 1535, 1455, 1315, 1130, 870.

NMR((CD$_3$)$_2$SO, δ ppm): 1.63(6H, s), 2.30(3H, s), 3.43(4H, s), 3.80–5.00(2H, br s), 5.30(2H, s), 6.80–7.50(6H, m), 8.20(1H, s).

EXAMPLE 4

2-[(4-tert-butylphenoxy)methyl]-5-methyl-4-piperidinopyridine m.p. 63°–64° C.

IR(KBr, cm$^{-1}$): 2960, 1600, 1520, 1260, 1050, 840.

NMR(CDCl$_3$, δ ppm): 1.26(9H, s), 1.62(6H, m), 2.20(3H, s), 2.80(4H, m), 5.02(2H, s), 6.82(2H, d, J=8 Hz), 7.05(1H, s), 7.25(2H, d, J=8 Hz), 8.20(1H, s).

EXAMPLE 5

2-[(4-sec-butylphenoxy)methyl]-5-methyl-4-piperidinopyridine hydrochloride m.p. 96°–98° C.

IR(KBr, cm$^{-1}$): 2932, 1644, 1596, 1515, 1494, 1458, 1257, 1227, 840.

NMR(CDCl$_3$, δ ppm): 0.79(3H, t, J=7 Hz), 1.15 (3H, d, J=7 Hz), 1.40–2.00(8H, m), 2.28(3H, s), 2.20–2.70(1H, m), 5.37(2H, s), 6.80–7.20(5H, m), 8.00(1H, s).

EXAMPLE 6

2-[(4-cyclopentylphenoxy)methyl]-5-methyl-4-piperidinopyridine m.p. 47°–49° C.

IR(KBr, cm$^{-1}$): 2950, 1600, 1460, 1250, 1050, 830.

NMR(CDCl$_3$, δ ppm): 1.20–2.40(14H, m), 2.19 (3H, s), 2.90(5H, m), 5.03(2H, s), 6.70–7.20(6H, m).

EXAMPLE 7

2-[(4-cyclohexylphenoxy)methyl]-5-methyl-4-piperidinopyridine m.p. 64°–68° C.

IR(KBr, cm$^{-1}$): 2926, 1596, 1518, 1455, 1251, 1065, 822.

NMR(CDCl$_3$, δ ppm): 1.10–2.10(17H, m), 2.20 (3H, s), 2.80–3.20(4H, m), 5.07(2H, s), 6.80–7.20(5H, m), 8.18(1H, s).

EXAMPLE 8

2-[(4-biphenylyl)oxymethyl]-5-methyl-4-piperidinopyridine m.p. 83°–84° C.

IR(KBr, cm$^{-1}$): 2932, 1599, 1524, 1272, 1062, 760.

NMR(CDCl$_3$, δ ppm): 1.52(6H, m), 2.20(3H, s), 2.93(4H, m), 6.90–7.70(10H, m), 8.21(1H, s).

EXAMPLE 9

2-[(4-biphenylyl)oxymethyl]-4-methoxy-5-methylpyridine m.p. 113°–114° C.

IR(KBr, cm$^{-1}$): 3070, 3020, 2930, 1600, 1580, 1495, 1380, 1190, 1150, 1060, 830, 765.

NMR(CDCl$_3$, δ ppm): 2.12(3H, s), 3.80(3H, s), 5.15(2H, s), 6.80–7.60(10H, m), 8.20(1H, s).

EXAMPLE 10

Production of 2-anilinomethyl-5-methyl-4-piperidinopiperidine:

A suspension of 186 mg (2.00 mmole) of aniline, 261 mg (1.00 mmole) of 2-chloromethyl-5-methyl-4-piperidinopyridine hydrochloride and 138 mg (1.00 mmole) of potassium carbonate in 10 ml of ethanol was heated under reflux for 10 hours. The solvent was evaporated under reduced pressure. After adding a saturated aqueous sodium chloride solution to the residue, and the mixture was extracted with methylene chloride. The methylene chloride layer was dried over anhydrous magnesium sulfate, and concentrated under reduced pressure. The residue was purified by silica gel column chromatography [eluted with chloroform/methanol (50/1)] to give 235 mg (yield 84%) of the captioned compound as crystals.

m.p. 109°–110° C.

IR(KBr, cm$^{-1}$): 3260, 3110, 2940, 1600, 1540, 1455, 1380, 1310, 745.

NMR(CDCl$_3$, δ ppm): 1.60(6H, br s), 2.88(4H, br s), 4.28 (2H, s), 3.90–4.50(1H, br), 6.50–7.30(6H, m), 8.11(1H, s).

EXAMPLE 11

In the same way as in Example 10, 2-[(N-methylanilino)methyl]-5-methyl-4-piperidinopyridine hydrochloride was produced.

m.p. 60°–62° C.

IR(KBr, cm$^{-1}$): 3320, 2930, 1635, 1545, 1515, 1240, 700.

NMR((CD$_3$)$_2$SO, δ ppm); 1.60(6H, br s), 2.28 (3H, s), 3.03(3H, s), 3.10–3.60(4H, m), 4.73(2H, s), 6.50–7.40(6H, m), 8.15(1H, s).

EXAMPLE 12

Production of 5-methyl-2-phenylthiomethyl-4-piperidinopyridine hydrochloride:

A 10% aqueous solution of sodium hydroxide (0.8 ml; 2.00 mmoles) was added to a solution of 160 mg (1.46 mmoles) of thiophenol and 211 mg (0.18 mmole) of 2-chloromethyl-5-methyl-4-piperidinopyridine hydrochloride in 3 ml of ethanol. The mixture was then stirred at room temperature for 1 hour. The solvent was evaporated under reduced pressure. After adding water to the residue, and the mixture was extracted with chloroform. The chloroform layer was dried over anhydrous magnesium sulfate, and concentrated under reduced pressure. The residue was purified by silica gel column chromatography (eluted with chloroform) to give the captioned compound as an oily free base. The oily base was dissolved in ether and treated with a 5% methanol solution of hydrogen chloride to give 226 mg (yield 75%) of the captioned compound as an oil.

Oil

IR(neat, cm$^{-1}$): 2940, 1595, 1390, 1095, 745, 700.

NMR(CDCl$_3$, δ ppm): 1.71(6H, m), 2.26(3H, s), 2.95(4H, m), 4.21(2H, s), 6.78(1H, s), 7.10–7.50(5H, m), 8.18(1H, s).

EXAMPLE 13

In the same way as in Example 12, 5-methyl-2-[(2-naphthyl)thiomethyl]-4-piperidinopyridine hydrochloride was produced.

Oil

IR(neat, cm$^{-1}$): 2940, 1600, 1500, 1380, 810.

NMR(CDCl$_3$, δ ppm): 1.50(6H, m), 2.12(3H, s), 2.75(4H, m), 4.20(2H, s), 6.65(1H, s), 7.20–7.85(7H, m), 8.13(1H, s).

EXAMPLE 14

Production of (E)-5-methyl-2-[2-(1-naphthyl)-vinyl]-4-piperidinopyridine hydrochloride (14-A) and (Z)-5-methyl-2-[2-(1-naphthyl)vinyl]-4-piperidinopyridine hydrochloride (14-B):

A suspension of 13.2 g (30.0 mmoles) of (1-naphthylmethyl)triphenylphosphonium chloride in 150 ml of tetrahydrofuran was cooled to about −30° C. in a cooling bath, and under a stream of nitrogen, 23.2 ml of a 1.55M hexane solution of n-butyllithium was added dropwise. The reaction mixture was further stirred at the above temperature for 0.5 hour, and a solution of 6.2 g (30.0 mmoles) of 5-methyl-4-piperidino-2-pyridinecarbaldehyde in 30 ml of tetrahydrofuran was added dropwise. After the addition, the cooling bath was removed, and the temperature was raised to room temperature. The mixture was further stirred at room temperature for 1 hour. Water (30 ml) was added to the reaction mixture, and tetrahydrofuran was evaporated under reduced pressure. The remaining aqueous layer was extracted with ether. The ether layer was washed with a saturated aqueous sodium chloride solution, and dried over anhydrous magnesium sulfate. The solvent was evaporated under reduced pressure. Hexane (500 ml) was added to the residue. The precipitated triphenylphosphine oxide was removed by filtration, and the filtrate was concentrated under reduced pressure to give a crude mixture of (E)- and (Z)-5-methyl-2-[2-(1-naphthyl)vinyl]-4-piperidinopyridines. The crude mixture was purified by silic gel column chromatography (eluted with hexane/ethyl acetate=2/1). The resulting (E)- and (Z)-isomers were each treated with an ethanol solution of hydrogen chloride, and then recrystallized from methanol/ether to give 4.5 g (yield 41%) of the captioned compound (14-A) and 3.7 g (yield 37%) of the captioned compound (14-B) as crystals.

Physical property data of (E)-5-methyl-2-[2-(1-naphthyl)vinyl]-4-piperidinopyridine hydrochloride (14-A) were as follows:

m.p. 210°–212° C.

IR(KBr, cm$^{-1}$): 2940, 2860, 1650, 1600, 1450, 1230, 1130, 780.

NMR(CDCl$_3$, δ ppm): 1.60(6H, m), 2.10(3H, s), 3.30(4H, m), 6.90–8.60(11H, m).

Physical property data of (Z)-5-methyl-2-[2-(1-naphthyl)vinyl]-4-piperidinopyridine hydrochloride (14-B) were as follows:

m.p. 181°–184° C.

IR(KBr, cm$^{-1}$): 2932, 1611, 1593, 1530, 1482, 1449, 1239, 786.

NMR(CD$_3$OD, δ ppm): 1.20–1.30(4H, m), 1.40–1.60(2H, m), 2.22(3H, s), 2.80–2.90 (4H, m), 6.32(1H, s), 6.88(1H, d, J=12 Hz), 7.38(1H, d, J=7 Hz), 7.52(1H, t, J=7 Hz), 7.50–7.60(2H, m), 7.74(1H, d, J=12 Hz), 7.90–8.00(3H, m), 7.97(1H, s).

EXAMPLES 15–61

In the same way as in Example 14, the following compounds of Examples 15 to 61 were obtained.

EXAMPLE 15

(E)-2-[2-(2-methoxy-1-naphthyl)vinyl]-5-methyl-4-piperidinopyridine hydrochloride m.p. 185°–186° C.

IR(CHCl$_3$, free base, cm$^{-1}$): 2940, 1590, 1250, 1120, 810, 670, 545.

NMR(CDCl$_3$, free base, δ ppm): 1.66(6H, m), 2.13(3H, s), 2.95(4H, m), 3.93(3H, s), 6.91(1H, s), 7.00–7.95(8H, m), 8.15–8.45(2H, m).

EXAMPLE 16

(A) (E)-2-[2-(4-methyl-1-naphthyl)vinyl]-5-methyl-4-piperidinopyridine m.p. 103°–106° C.

IR(KBr, cm$^{-1}$): 2932, 1584, 1491, 1386, 969, 753.

NMR(CDCl$_3$, δ ppm): 1.40–1.90(6H, m), 2.21(3H, s), 2.64(3H, s), 2.70–3.10(4H, m), 6.88(1H, s), 7.20–8.50(8H, m), 7.07(1H, d, J=16 Hz).

(B) (Z)-2-[2-(4-methyl-1-naphthyl)vinyl]-5-methyl-4-piperidinopyridine hydrochloride m.p. 186°–189° C.

IR(KBr, cm$^{-1}$): 2938, 1638, 1626, 1599, 1533, 1497, 1449, 1239, 768.

NMR(CDCl$_3$, δ ppm): 0.90–1.60(6H, m), 2.12 (3H, s), 2.40–2.80(4H, m), 2.68(3H, s), 6.11(1H, s), 7.10–8.20(9H, m).

EXAMPLE 17

(A) (E)-2-[2-(4-chloro-1-naphthyl)vinyl]-5-methyl-4-piperidinopyridine m.p. 119°–122° C.

IR(KBr, cm$^{-1}$): 2938, 1584, 1491, 1386, 969, 930, 822, 753.

NMR(CDCl₃, δppm): 1.40–1.90(6H, m), 2.21(3H, s), 2.70–3.10(4H, m), 6.83(1H, s), 7.04(1H, d, J=16 Hz), 7.20–7.80(4H, m), 8.10–8.50(4H, m).

(B) (Z)-2-[2-(4-chloro-1-naphthyl)vinyl]-5-methyl-4-piperidinopyridine hydrochloride
m.p. 201°–203° C.
IR(KBr, cm⁻¹): 2944, 2554, 1626, 1605, 1533, 1449, 1374, 1242.
NMR(CDCl₃, δppm): 0.90–1.60(6H, m), 2.16(3H, s), 2.40–2.90(4H, m), 6.02(1H, s), 7.20–8.40(9H, m).

EXAMPLE 18

(A) (E)-2-[2-(4-fluoro-1-naphthyl)vinyl]-5-methyl-4-piperidinopyridine hydrochloride
m.p. 238°–239° C.
IR(KBr, cm⁻¹): 3418, 2938, 1617, 1578, 1476, 1389, 1275, 978.
NMR(CDCl₃, δppm): 1.60–1.90(6H, m), 2.09(3H, s), 3.26(4H, s), 6.86(1H, s), 7.00–8.20(7H, m), 8.74(1H, d, J=9 Hz), 8.92(1H, d, J=15 Hz).

(B) (Z)-2-[2-(4-fluoro-1-naphthyl)vinyl]-5-methyl-4-piperidinopyridine hydrochloride
m.p. 195°–197° C.
IR(KBr, cm⁻¹): 3436, 2854, 1602, 1485, 1311, 1053, 918.
NMR(CDCl₃, δppm): 1.20–1.40(4H, m), 1.40–1.60(2H, m), 2.16(3H, s), 2.50–2.75 (4H, m), 6.12(1H, s), 7.10–8.20(9H, m).

EXAMPLE 19

(A) (E)-2-[2-(4-methoxy-1-naphthyl)vinyl]-5-methyl-4-piperidinopyridine hydrochloride
m.p. 223°–225° C.
IR(KBr, cm⁻¹): 2932, 2752, 1620, 1578, 1449, 1362, 1284, 1095.
NMR(CDCl₃, δppm): 1.72(6H, s), 2.13(3H, s), 3.26(4H, s), 4.03(3H, s), 6.80–8.82(10H, m).

(B) (Z)-2-[2-(4-methoxy-1-naphthyl)vinyl]-5-methyl-4-piperidinopyridine
m.p. 100°–102° C.
IR(KBr, cm⁻¹): 3004, 2842, 1539, 1488, 1446, 1401, 1359, 1161, 1095, 768.
NMR(CDCl₃, δppm): 1.33(6H, br s), 2.07(3H, s), 2.00–2.50(4H, m), 3.94(3H, s), 6.28(1H, s), 6.40–7.70(4H, m), 7.70–8.50(3H, m).

EXAMPLE 20

(A) (E)-2-[2-(5-methyl-1-naphthyl)vinyl]-5-methyl-4-piperidinopyridine
m.p. 108°–110° C.
IR(KBr, cm⁻¹): 2944, 1584, 1491, 1386, 963, 786.
NMR(CDCl₃, δppm): 1.40–2.00(6H, m), 2.20(3H, s), 2.66(3H, s), 2.80–3.20(4H, m), 6.88(1H, s), 7.08(1H, d, J=15 Hz), 7.30–8.50(7H, m), 8.27(1H, s).

(B) (Z)-2-[2-(5-methyl-1-naphthyl)vinyl]-5-methyl-4-piperidinopyridine hydrochloride
m.p. 194°–197° C.
IR(KBr, cm⁻¹): 2944, 2500, 1626, 1599, 1530, 1482, 1449, 1386, 1239, 795.
NMR(CDCl₃, δppm): 1.00–1.70(6H, m), 2.16(3H, s), 2.40–2.70(4H, m), 2.70(3H, s), 6.10(1H, s), 7.20–8.20(9H, m).

EXAMPLE 21

(A) (E)-2-[2-(5-methoxy-1-naphthyl)vinyl]-5-methyl-4-piperidinopyridine
m.p. 140°–141° C.
IR(KBr, cm⁻¹): 3080, 3060, 2930, 2860, 2815, 1585, 1495, 1475, 1410, 1035, 780.
NMR(CDCl₃, δppm): 1.50–1.80(6H, m), 2.22(3H, s), 2.80–3.10(4H, m), 3.92(3H, s), 6.70–8.50(10H, m).

(B) (Z)-2-[2-(5-methoxy-1-naphthyl)vinyl]-5-methyl-4-piperidinopyridine hydrochloride
m.p. 199°–201° C.
IR(KBr, cm⁻¹): 3450, 3020, 2940, 2745, 1650, 1600, 1535, 1445, 1390, 1240, 1035, 795.
NMR(CDCl₃, δppm): 1.10–1.50(6H, m), 2.12(2H, s), 2.40–2.70(4H, m), 3.98(3H, s), 6.11(1H, s), 6.70–8.40(9H, m).

EXAMPLE 22

(A) (E)-2-[2-(8-methyl-1-naphthyl)vinyl]-5-methyl-4-piperidinopyridine hydrochloride
m.p. 72°–75° C.
IR(KBr, cm⁻¹): 2938, 1584, 1542, 1494, 1455, 1386, 1224, 975, 810, 771.
NMR(CDCl₃, δppm): 1.40–2.00(6H, m), 2.20(3H, s), 2.87(3H, s), 2.70–3.20(4H, m), 6.70(1H, d, J=16 Hz), 6.82(1H, s), 7.00–7.90(6H, m), 8.24(1H, s), 8.40(1H, d, J=16 Hz).

(B) (Z)-2-[2-(8-methyl-1-naphthyl)vinyl]-5-methyl-4-piperidinopyridine
m.p. 108°–110° C.
IR(KBr, cm⁻¹): 2938, 1584, 1488, 1446, 1383, 1242, 768.
NMR(CDCl₃, δppm): 1.10–1.60(6H, m), 2.01(3H, s), 1.80–2.30(4H, m), 2.81(3H, s), 6.04(1H, s), 6.70(1H, d, J=12 Hz), 7.00–7.80(7H, m), 8.08(1H, s).

EXAMPLE 23

(A) (E)-5-methyl-2-[2-(1-naphthyl)vinyl]pyridine
m.p. 185°–187° C.
IR(KBr, cm⁻¹): 2450, 1610, 1450, 1390, 800, 780.
NMR(CDCl₃, free base, δppm): 2.25(3H, s), 7.25–7.85(9H, m), 8.15–8.55(2H, m).

(B) (Z)-5-methyl-2-[2-(1-naphthyl)vinyl]pyridine hydrochloride
m.p. 140°–143° C.
IR(KBr, cm⁻¹): 2310, 2050, 1600, 1550, 1260, 800.
NMR(CDCl₃, free base, δppm): 2.03(3H, s), 6.50–8.05(11H, m), 8.30(1H, s).

EXAMPLE 24

(A) (E)-4-methoxy-5-methyl-2-[2-(1-naphthyl)vinyl]pyridine
m.p. 111°–112° C.
IR(KBr, cm⁻¹): 3060, 2980, 1590, 1500, 1445, 1300, 1150, 1030, 965, 775.
NMR(CDCl₃, δppm): 2.16(3H, s), 3.84(3H, s), 6.81(1H, s), 7.11(1H, d, J=16 Hz), 7.20–7.90(7H, m), 8.25(1H, s), 8.38(1H, d, J=16 Hz).

(B) (Z)-4-methoxy-5-methyl-2-[2-(1-naphthyl)vinyl]pyridine hydrochloride
m.p. 155°–157° C.
IR(neat, free base, cm⁻¹): 3060, 3020, 2930, 1595, 1500, 1380, 1255, 1040, 795.
NMR(CDCl₃, δppm): 2.00(3H, s). 2.90(3H, s), 6.16(1H, s), 6.92(1H, d, J=12 Hz), 7.10–8.10(8H, m), 8.13(1H, s).

EXAMPLE 25

(A) (E)-5-methyl-2-[2-(1-naphthyl)vinyl]-4-propoxypyridine
m.p. 95°–97° C.

IR(KBr, cm$^{-1}$): 3050, 2960, 2930, 2870, 1595, 1495, 1300, 1025, 1010, 795.

NMR(CDCl$_3$, δppm): 1.10(3H, t, J=8 Hz), 1.90(2H, m), 2.22(3H, s), 4.06(2H, t, J=7 Hz), 6.88(1H, s), 7.16(1H, d, J=16 Hz), 7.46–7.58(3H, m), 7.78–7.89(3H, m), 8.30(1H, s), 8.29–8.34(1H, m), 8.37(1H, d, J=11 Hz).

(B) (Z)-5-methyl-2-[2-(1-naphthyl)vinyl]-4-propoxypyridine hydrochloride
m.p. 143°–145° C.

IR(KBr, cm$^{-1}$): 3450, 3050, 2960, 1640, 1610, 1475, 1320, 1305, 1240, 970.

NMR(CDCl$_3$, δppm): 0.71(3H, t, J=7 Hz), 1.25–1.36(2H, m), 2.07(3H, s), 2.95(2H, t, J=7 Hz), 6.21(1H, s), 7.26(1H, d, J=12 Hz), 7.36–7.57(5H, m), 7.84(1H, d, J=7 Hz), 7.89(1H, dd, J=2, 7 Hz), 8.00(1H, dd, J=3, 7 Hz), 8.17(1H, s).

EXAMPLE 26

(A) (E)-4-isopentyloxy-5-methyl-2-[2-(1-naphthyl)vinyl]pyridine
m.p. 82°–84° C.

IR(KBr, cm$^{-1}$): 3055, 3010, 2955, 1930, 1870, 1595, 1475, 1300, 1150, 1030, 795.

NMR(CDCl$_3$, δppm): 1.01(6H, d, J=7 Hz), 1.76(2H, q, J=7 Hz), 1.83–1.97(1H, m), 2.21(3H, s), 4.13(2H, t, J=7 Hz), 6.89(1H, s), 7.17(1H, d, J=16 Hz), 7.46–7.57(3H, m), 7.80(1H, d, J=7 Hz), 7.82(1H, d, J=8 Hz), 7.87(1H, dd, J=2, 7 Hz), 8.29(1H, s), 8.31–8.35(1H, m), 8.37(1H, d, J=16 Hz).

(B) (Z)-4-isopentyloxy-5-methyl-2-[2-(1-naphthyl)vinyl]pyridine hydrochloride
m.p. 94°–96° C.

IR(KBr, cm$^{-1}$): 3520, 3470, 3045, 3010, 2955, 2650, 1620, 1380, 1240, 790.

NMR(CDCl$_3$, δppm): 0.74(6H, d, J=7 Hz), 1.21–1.29(2H, m), 1.39–1.48(1H, m), 2.07(3 H, s), 3.00(2H, t, J=7 Hz), 6.23(1H, s), 7.31–7.62(6H, m), 7.85(1H, d, J=9 Hz), 7.89(1H, dd, J=3, 6 Hz) 7.95(1H, dd, J=2, 7 Hz), 8.17(1H, s).

EXAMPLE 27

(A) (E)-5-methyl-2-[2-(1-naphthyl)vinyl]-4-pentyloxypyridine hydrochloride
m.p. 84°–86° C.

IR(KBr, cm$^{-1}$): 3400, 2950, 1620, 1450, 1340, 1160, 800, 775.

NMR(CD$_3$OD, δppm): 1.00(3H, t, J=7 Hz), 1.40–1.60(4H, m), 1.95(2H, m), 2.26(3H, s), 4.42(2H, t, J=6 Hz), 7.31(1H, d, J=16 Hz), 7.52–7.68(4H, m), 7.77(1H, s), 7.92(1H, d, J=6 Hz), 7.96(1H, d, J=8 Hz), 8.26(1H, s), 8.43(1H, d, J=8 Hz), 8.72(1H, d, J=16 Hz).

(B) (Z)-5-methyl-2-[2-(1-naphthyl)vinyl]-4-pentyloxypyridine hydrochloride
m.p. 94°–96° C.

IR(KBr, cm$^{-1}$): 2950, 2650, 1620, 1475, 1320, 1240, 800.

NMR(CD$_3$OD, δppm): 0.86(3H, t, J=7 Hz), 1.15(2H, m), 1.42(2H, m), 2.15(3H, s), 3.38(2H, t, J=7 Hz), 6.61(1H, s), 7.01(1H, d, J=12 Hz), 7.36–7.62(4H, m), 7.87(1H, d, J=12 Hz), 7.92–8.20(3H, m), 8.29(1H, s).

EXAMPLE 28

(A) (E)-4-cyclohexyloxy-5-methyl-2-[2-(1-naphthyl)vinyl]pyridine
m.p. 106°–109° C.

IR(KBr, cm$^{-1}$): 2938, 1590, 1491, 1293, 1143, 792, 777.

NMR(CDCl$_3$, δppm): 1.35–1.55(3H, m), 1.55–1.73(3H, m), 1.73–1.90(2H, m), 1.90–2.05(2H, m), 2.20(3H, s), 4.40–4.50(1H, m), 6.85(1H, s), 7.15(1H, d, J=16 Hz), 7.50(1H, dd, J=8, 8 Hz), 7.50(1H, dt, J=2, 8 Hz), 7.55(1H, dt, J=2, 8 Hz), 7.80(1H, d, J=8 Hz), 7.82(1H, d, J=8 Hz), 7.87(1H, dd, J=2, 7 Hz), 8.30(1H, s), 8.33(1H, dd, J=2, 8 Hz), 8.38(1H, d, J=16 Hz).

(B) (Z)-4-cyclohexyloxy-5-methyl-2-[2-(1-naphthyl)vinyl]pyridine
m.p. 88°–91° C.

IR(KBr, cm$^{-1}$): 2932, 1593, 1491, 1278, 1251, 786.

NMR(CDCl$_3$, δppm): 0.76–0.86(2H, m), 0.94–1.21 (5H, m), 1.33–1.48(3H, m), 2.01(3H, s), 3.09–3.15(1H, m), 6.13(1H, s), 6.96(1H, d, J=13 Hz), 7.22(1H, d, J=13 Hz), 7.36(1H, dd, J=12, 8 Hz), 7.41(1H, t, J=8 Hz), 7.46(1H, dt, J=2, 7 Hz), 7.50(1H, dt, J=2, 7 Hz), 7.78(1H, d, J=8 Hz), 7.86(1H, dd, J=2, 7 Hz), 8.05(1H, dd, J=2,7 Hz), 8.16(1H, s).

EXAMPLE 29

(A) (E)-(5-methyl-2-[2-(1-napthyl)vinyl]-4-phenoxypyridine
m.p. 112°–116° C.

IR(KBr, cm$^{-1}$): 1590, 1560, 1491, 1281, 1203, 960, 774.

NMR(CDCl$_3$, δppm): 2.35(3H, s), 6.71(1H, s), 7.03(1H, d, J=16 Hz), 7.11(2H, d, J=8 Hz), 7.23(1H, t, J=8 Hz), 7.40–7.56(5H, m), 7.73(1H, d, J=7 Hz), 7.80(1H, d, J=8 Hz), 7.85(1H, dd, J=2, 7 Hz), 8.26(1H, dd, J=2, 7 Hz), 8.34(1H, d, J=16 Hz), 8.45(1H, s).

(B) (Z)-5-methyl-2-[2-(1-naphthyl)vinyl]-4-phenoxypyridine hydrochloride
m.p. 166°–168° C.

IR(KBr, cm$^{-1}$): 2380, 1617, 1491, 1473, 1308, 1242, 1203, 798.

NMR(CD$_3$OD, δppm): 2.33(3H, s), 6.13(1H, s), 6.44–6.52(2H, m), 6.89(1H, d, J=12 Hz), 7.01–7.09(3H, m), 7.17(1H, d, J=7 Hz), 7.31(1H, dd, J=7, 8 Hz), 7.42(1H, ddd, J=1, 7, 8 Hz), 7.53(1H, ddd, J=1, 7, 8 Hz), 7.62(1H, d, J=12 Hz), 7.75(1H, d, J=8 Hz), 7.82(1H, d, J=8 Hz), 7.91(1H, d, J=8 Hz), 8.46(1H, s).

EXAMPLE 30

(A) (E)-4-benzyloxy-5-methyl-2-[2-(1-naphthyl)vinyl]pyridine hydrochloride
m.p. 145°–148° C.

IR(KBr, cm$^{-1}$): 3436, 1644, 1620, 1476, 1449, 1341, 1161.

NMR(CD$_3$OD, δppm): 2.28(3H, s), 5.51(2H, s), 7.31(1H, d, J=16 Hz), 7.40–7.50(4H, m), 7.50–7.60(3H, m), 7.64(1H, dt, J=1, 8 Hz), 7.90–8.00(4H, m), 8.28(1H, s), 8.43(1H, d, J=8 Hz), 8.71(1H, d, J=16 Hz).

(B) (Z)-4-benzyloxy-5-methyl-2-[2-(1-naphthyl)vinyl]pyridine hydrochloride
m.p. 136°–138° C.

IR(KBr, cm$^{-1}$): 2434, 1620, 1482, 1452, 1317, 1242, 795.

NMR(CD$_3$OD, δppm): 2.22(3H, s), 4.55(2H, s), 6.75(1H, s), 6.85(2H, dd, J=1, 7 Hz), 6.95(1H, d, J=12 Hz), 7.16(2H, dt, J=1, 7 Hz), 7.24(1H, t, J=7 Hz), 7.39(1H, dd, J=1, 7 Hz), 7.49(1H, dd, J=7, 8 Hz), 7.58–7.68(2H, m), 7.87(1H, d, J=12 Hz), 7.97–8.04(3H, m), 8.33(1H, s).

EXAMPLE 31

(A) (E)-5-methyl-2-[2-(1-naphthyl)vinyl]-4-phenethyloxypyridine
m.p. 112°–113° C.

IR(KBr, cm$^{-1}$): 3050, 2945, 1590, 1495, 1370, 1230, 1150, 1025, 960, 795, 755.

NMR(CD$_3$OD, δppm): 2.20(3H, s), 3.18(2H, t, J=7 Hz), 4.31(2H, t, J=7 Hz), 6.87(1H, s), 7.14(1H, d, J=16 Hz), 7.24–7.39(5H, m), 7.45–7.55(3H, m), 7.79(1H, d, J=8 Hz), 7.82(1H, d, J=9 Hz), 7.86(1H, dd, J=2, 7 Hz), 8.29(1H, s), 8.31(1H, d, J=9 Hz), 8.35(1H, d, J=16 Hz).

(B) (Z)-5-methyl-2-[2-(1-naphthyl)vinyl]-4-phenethyloxypyridine hydrochloride m.p. 163°–164° C.

IR(KBr, cm$^{-1}$): 3440, 2930, 2470, 1615, 1485, 1380, 1245, 1160, 1145, 1025, 775.

NMR(CDCl$_3$, δppm): 2.06(3H, s), 2.68(2H, t, J=7 Hz), 3.12(2H, t, J=7 Hz), 6.21(1H, s), 6.89–6.94(2H, m), 7.22–7.36(4H, m), 7.41(1H, dd, J=7, 8 Hz), 7.45–7.53(2H, m), 7.49(1H, d, J=12 Hz), 7.66(1H, d, J=12 Hz), 7.68–7.74(2H, m), 7.88–7.92(1H, m), 8.16(1H, s).

EXAMPLE 32

(A) (E)-4-cyclohexylthio-5-methyl-2-[2-(1-naphthyl)vinyl]pyridine hydrochloride m.p. 178°–181° C.

IR(KBr, cm$^{-1}$): 3442, 2932, 2854, 1638, 1611, 1437.

NMR(CD$_3$OD, δppm): 1.35–1.53(1H, m), 1.53–1.80(5H, m), 1.80–1.95(2H, m), 2.12–2.28(2H, m), 2.33(3H, s), 3.88–4.00(1H, m), 7.39(1H, d, J=16 Hz), 7.65(1H, d, J=8 Hz), 7.57(1H, dd, J=1, 8 Hz), 7.63(1H, ddd, J=1, 7, 8 Hz), 7.93(1H, s), 7.93(1H, d, J=9 Hz), 7.96(1H, d, J=8 Hz), 7.99(1H, d, J=7 Hz), 8.20(1H, d, J=1 Hz), 8.39(1H, d, J=9 Hz), 8.67(1H, d, J=16 Hz).

(B) (Z)-4-cyclohexylthio-5-methyl-2-[2-(1-naphthyl)vinyl]pyridine m.p. 106°–109° C.

IR(KBr, cm$^{-1}$): 2992, 2854, 1575, 1476, 1452, 870, 789, 774.

NMR(CDCl$_3$, δppm): 0.54–0.73(2H, m), 0.91–1.12(3H, m), 1.20–1.46(5H, m), 1.98–2.13(1H, m), 2.11(3H, s), 6.58(1H, s), 6.95(1H, d, J=12 Hz), 7.25(1H, d, J=12 Hz), 7.34(1H, dt, J=6, 1 Hz), 7.38(1H, t, J=7 Hz), 7.46–7.55(2H, m), 7.78(1H, d, J=9 Hz), 7.84–7.90(1H, m), 8.04–8.10(1H, m), 8.18(1H, s).

EXAMPLE 33

(A) (E)-4-dimethylamino-5-methyl-2-[2-(1-naphthyl)vinyl]pyridine hydrochloride m.p. >270° C.

IR(KBr, cm$^{-1}$): 2896, 2722, 1647, 1623, 1599, 1548, 1440.

NMR(CDCl$_3$+CD$_3$OD, δppm): 2.23(6H, s), 2.36(3H, s), 6.90–8.70(11H, m).

(B) (Z)-4-dimethylamino-5-methyl-2-[2-(1-naphthyl)vinyl]pyridine hydrochloride m.p. 105°–108° C.

IR(KBr, cm$^{-1}$): 2770, 1647, 1626, 1605, 1545, 1518, 1419, 798.

NMR(CDCl$_3$, δppm): 2.27(3H, s), 2.47(6H, s), 6.02(1H, s), 7.20–8.10(10H, m).

EXAMPLE 34

(A) (E)-5-methyl-2-[2-(1-naphthyl)vinyl]-4-(pyrrolidin-1-yl)pyridine hydrochloride m.p. 245° C. (decomposition)

IR(KBr, cm$^{-1}$): 2794, 1674, 1626, 1599, 1539, 1482, 1464.

NMR(CDCl$_3$+CD$_3$OD, δppm): 1.70–2.20(4H, m), 2.09(3H, s), 3.30–3.70(4H, m), 6.49(1H, s), 7.01(1H, d, J=17 Hz), 7.20–8.40(8H, m), 8.31(1H, d, J=17 Hz).

(B) (Z)-5-methyl-2-[2-(1-naphthyl)vinyl]-4-(pyrrolidin-1-yl)pyridine hydrochloride m.p. 204°–207° C.

IR(KBr, cm$^{-1}$): 2872, 2776, 1647, 1626, 1599, 1539, 1506, 1485, 1461.

NMR(CDCl$_3$, δppm): 1.50–1.90(4H, m), 2.33(3H, s), 2.60–3.10(4H, m), 5.83(1H, s), 7.20(1H, d, J=12 Hz), 7.30–8.10(9H, m).

EXAMPLE 35

(A) (E)-5-methyl-4-morpholino-2-[2-(1-naphthyl)vinyl]pyridine m.p. 111°–114° C.

IR(KBr, cm$^{-1}$): 2962, 2832, 1587, 1494, 1449, 1116, 1005, 972, 795.

NMR(CDCl$_3$, δppm): 2.22(3H, s), 2.80–3.20(4H, m), 3.60–4.00(4H, m), 6.89(1H, s), 7.12(1H, d, J=15 Hz), 7.20–8.00(7H, m), 8.10–8.40(2H, m), 8.39(1H, d, J=15 Hz).

(B) (Z)-5-methyl-4-morpholino-2-[2-(1-naphthyl)vinyl]pyridine hydrochloride m.p. 206°–208° C.

IR(KBr, cm$^{-1}$): 2854, 2656, 1647, 1623, 1602, 1536, 1485, 1443, 1239, 1119, 798.

NMR(CDCl$_3$, δ ppm): 2.20 (3H, s), 2.40–2.80(4H, m), 3.20–3.60(4H, m), 6.13(1H, s), 7.20–8.20(10H, m).

EXAMPLE 36

(A) (E)-5-methyl-4-(4-methylpiperazin-1-yl)-2-[2-(1-naphthyl)vinyl]pyridine hydrochloride m.p. 235° C. (decomposition)

IR(KBr, cm$^{-1}$): 3412, 2920, 2680, 1644, 1626, 1530, 1473, 1452, 975.

NMR(CD$_3$OD, δ ppm): 2.33(3H, s), 3.03(3H, s), 3.40–3.90(8H, s), 7.26(1H, d, J=15 Hz), 7.50–8.50(9H, m), 8.15(1H, d, J=15 Hz).

(B) (Z)-5-methyl-4-(4-methylpiperazin-1-yl)-2-[2-(1-naphthyl)vinyl]pyridine hydrochloride m.p. 245° C. (decomposition)

IR(KBr, cm$^{-1}$): 3442, 2680, 1623, 1605, 1533, 1479, 1455, 1245.

NMR(CD$_3$OD, δ ppm): 2.29(3H, s), 2.85(3H, s). 2.90–3.50(8H, m), 6.50(1H, s), 6.98(1H, d, J=12 Hz), 7.30–8.30(9H, m).

EXAMPLE 37

(A) (E)-5-methyl-2-[2-(1-naphthyl)vinyl]-4-(perhydroazepin-1-yl)pyridine hydrochloride m.p. 200°–203° C.

IR(KBr, cm$^{-1}$): 2926, 1644, 1620, 1596, 1530, 1449.

NMR(CD$_3$OD, δ ppm): 1.60–1.80(4H, m), 1.80–2.00(4H, m), 2.48(3H, d, J=3 Hz), 3.70–3.90(4H, m), 7.12(1H, d, J=4 Hz), 7.23(1H, dd, J=1,17 Hz), 7.50–7.70(4H, m), 7.80–8.00(3H, m), 8.35(1H, d, J=9 Hz).

(B) (Z)-5-methyl-2-[2-naphthyl)vinyl]-4-(perhydroazepin-1-yl)pyridine hydrochloride m.p. 179°–180° C.

IR(KBr, cm$^{-1}$): 3450, 3030, 2925, 2850, 2700, 1625, 1595, 1535, 1380, 1240, 795.

NMR(CDCl$_3$, δ ppm): 1.06–1.08(4H, m), 1.20–1.25(4H, m), 2.27(3H, s), 2.95(4H, t, J=6 Hz), 6.03(1H, s), 7.31–7.35(1H, m), 7.33(1H, d, J=12 Hz), 7.41–7.55(4H, m), 7.80–7.93(4H, m).

EXAMPLE 38

(A) (E)-5-methyl-4-(4-methylpiperidino)-2-[2-(1-naphthyl)vinyl]pyridine hydrochloride
m.p. 239°–240° C.
IR(KBr, cm$^{-1}$): 3412, 3052, 2914, 1644, 1530, 1458, 1359, 1254, 1194, 972, 774.
NMR(CDCl$_3$, δ ppm): 1.02(3H, d, J=6 Hz), 1.20–1.40(2H, m), 1.50–1.90(4H, m), 2.06(3H, s), 2.84(2H, t, J=13 Hz), 3.62(2H, d, J=13 Hz), 6.93(1H, s), 7.15–7.97(8H, m), 8.68(1H, d, J=8 Hz), 8.93(1H, d, J=16 Hz).

(B) (Z)-5-methyl-4-(4-methylpiperidino)-2-[2-(1-naphthyl)vinyl]pyridine hydrochloride
m.p. 189°–190° C.
IR(KBr, cm$^{-1}$): 3046, 2842, 1641, 1602, 1482, 1386, 1251, 1131, 792.
NMR(CDCl$_3$, δ ppm): 0.40–1.00(5H, m), 1.35(2H, d, J=13 Hz), 1.70(1H, br s), 2.16(3H, s), 2.35(2H, t, J=13 Hz), 2.77(2H, d, J=13 Hz), 6.12(1H, s), 7.20–8.10(10H, m).

EXAMPLE 39

(A) (E)-5-methyl-4-(3-methylpiperidino)-2-[2-(1-naphthyl)vinyl]pyridine hydrochloride
m.p. 201°–204° C.
IR(KBr, cm$^{-1}$): 2926, 1644, 1620, 1530, 1446, 1230.
NMR(CD$_3$OD, δ ppm): 1.01(3H, d, J=7 Hz), 1.18–1.37(1H, m), 1.63–2.03(4H, m), 2.34(3H, s), 2.80(1H, dd, J=11,13 Hz), 3.10(1H, t, J=11 Hz), 3.82(2H, dt, J=2,16 Hz), 7.23(1H, d, J=16 Hz), 7.32(1H, s), 7.55(2H, t, J=8 Hz), 7.62(1H, ddd, J=2,7,9 Hz), 7.83–8.02(4H, m), 8.38(1H, d, J=9 Hz), 8.52(1H, d, J=16 Hz).

(B) (Z)-5-methyl-4-(3-methylpiperidino)-2-[2-(1-naphthyl)vinyl]pyridine hydrochloride
m.p. 143°–147° C.
IR(KBr, cm$^{-1}$): 2926, 2614, 1623, 1602, 1533, 1494, 1446, 1242.
NMR(CD$_3$OD, δ ppm): 0.61(3H, d, J=7 Hz), 0.80–1.32(4H, m), 1.37–1.48(1H, m), 1.57–1.70(1H, m), 2.22(3H, s), 2.52–2.65(1H, m), 2.80–2.90(1H, m), 3.17(1H, d, J=14 Hz), 6.30(1H, s), 6.88(1H, d, J=12 Hz), 7.38(1H, dt, J=7,1 Hz), 7.50(1H, dd, J=7,8 Hz), 7.50–7.60(2H, m), 7.73(1H, d, J=12 Hz), 7.91–8.01(4H, m).

EXAMPLE 40

(A) (E)-4-diethylamino-5-methyl-2-[2-(1-naphthyl)vinyl]pyridine hydrochloride
m.p. 193°–195° C.
IR(KBr, cm$^{-1}$): 2752, 1644, 1623, 1596, 1536, 1233.
NMR(CD$_3$OD, δ ppm): 1.32(3H, t, J=7 Hz), 2.43(3H, s), 3.67(2H, q, J=7 Hz), 7.10(1H, s), 7.23(1H, d, J=16 Hz), 7.50–7.70(3H, m), 7.90–8.00(4H, m), 8.36(1H, d, J=8 Hz), 8.45(1H, d, J=16 Hz).

(B) (Z)-4-diethylamino-5-methyl-2-[2-(1-naphthyl)vinyl]pyridine hydrochloride
m.p. 190°–192° C.
IR(KBr, cm$^{-1}$): 2740, 1647, 1626, 1602, 1533, 1509, 1488, 1356, 795.
NMR(CD$_3$OD, δ ppm): 0.68(3H, t, J=7 Hz), 2.32(3H, s), 3.00(2H, q, J=7 Hz), 6.19(1H, s), 6.84(1H, d, J=12 Hz), 7.36(1H, dd, J=1,7 Hz), 7.49(1H, dd, J=7,8 Hz), 7.50–7.60(2H, m), 7.69(1H, d, J=12 Hz), 7.87(1H, s), 7.92(1H, d, J=8 Hz), 7.90–8.00(2H, m).

EXAMPLE 41

(A) (E)-2-[2-(1-naphthyl)vinyl]-4-piperidinopyridine hydrochloride
m.p. 128°–130° C.
IR(KBr, cm$^{-1}$): 2930, 1650, 1540, 1220, 990, 780, 540.
NMR(CD$_3$OD, δ ppm): 1.63(6H, br s), 3.50(4H, br s), 6.63(1H, d, J=9 Hz), 6.80–7.30(2H, m), 7.35–8.00(7H, m), 8.20–8.60(2H, m)

(B) (Z)-2-[2-(1-naphthyl)vinyl]-4-piperidinopyridine hydrochloride
m.p. 130°–131° C.
IR(KBr, cm$^{-1}$): 3450, 2930, 2720, 1620, 1550, 1250, 790.
NMR(CD$_3$OD, δ ppm): 1.00–1.90(6H, m), 3.00(4H, m), 6.20(1H, d, J=12 Hz), 6.65–7.05(2H, m), 7.20–7.70(5H, m), 7.70–8.20(4H, m).

EXAMPLE 42

(A) (E)-5-ethyl-2-[2-(1-naphthyl)vinyl]-4-piperidinopyridine hydrochloride
m.p. 205°–207° C.
IR(KBr, cm$^{-1}$): 3430, 2940, 1645, 1620, 1520, 1475, 1220, 1125, 990, 800, 780.
NMR(CDCl$_3$, δ ppm): 1.10(3H, t, J=7 Hz), 1.40–1.90(6H, m), 2.29(2H, q, J=7 Hz), 2.90–3.30(4H, m), 6.90–9.00(11H, m).

(B) (Z)-5-ethyl-2-[2-(1-naphthyl)vinyl]-4-piperidinopyridine hydrochloride
m.p. 187°–190° C.
IR(KBr, cm$^{-1}$): 3460, 3010, 2940, 2520, 1650, 1625, 1495, 1440, 1020, 785.
NMR(CDCl$_3$, δ ppm): 1.18(3H, t, J=7 Hz), 1.00–1.60(6H, m), 2.44(2H, q, J=7 Hz), 2.30–2.80(4H, m), 6.22(1H, s), 7.30–8.10(10H, m).

EXAMPLE 43

(A) (E)-2-[2-(1-naphthyl)vinyl]-4-piperidino-5-propylpyridine hydrochloride
m.p. 174°–175° C.
IR(KBr, cm$^{-1}$): 3410, 3050, 2855, 1625, 1475, 1390, 1230, 1125, 980, 800, 775.
NMR(CDCl$_3$, free base, δ ppm): 0.97(3H, t, J=8 Hz), 1.40–2.00(8H, m), 2.40–2.80(2H, m), 2.80–3.20(4H, m), 6.90–8.10(11H, m).

(B) (Z)-2-[2-(1-naphthyl)vinyl]-4-piperidino-5-propylpyridine hydrochloride
m.p. 122°–125° C.
IR(KBr, cm$^{-1}$): 3400, 3050, 2940, 1645, 1600, 1520, 1470, 1240, 1020, 800, 780.
NMR(CDCl$_3$, free base, δ ppm): 1.40(3H, t, J=6 Hz), 1.10–1.80(8H, m), 1.90–2.60(6H, m), 6.28(1H, s), 6.70–8.30(10H, m).

EXAMPLE 44

(A) (E)-3-[2-(1-naphthyl)vinyl]-2-piperidinopyridine hydrochloride
m.p. 160°–162° C.
IR(KBr, cm$^{-1}$): 3430, 3030, 2930, 2850, 1595, 1540, 1425, 1335, 1210, 990, 935, 775.
NMR(CDCl$_3$, δ ppm): 1.70–1.73(2H, m), 1.79–1.82(4H, m), 3.60–3.63(6H, m), 7.02(1H, d, J=16 Hz), 7.13(1H, dd, J=6,8 Hz), 7.49–7.61(3H, m), 7.73(1H, d, J=7 Hz), 7.86–7.93(2H, m), 7.91(1H, d, J=16 Hz), 8.14–8.20(2H, m), 8.35(1H, dd, J=2,6 Hz).

(B) (Z)-3-[2-(1-naphthyl)vinyl]-2-piperidinopyridine hydrochloride
m.p. 145°–147° C.

IR(KBr, cm⁻¹): 3450, 3060, 2930, 1600, 1470, 1450, 1335, 1250, 1220, 940, 810, 770.

NMR(CDCl₃, δ ppm): 1.73–1.79(2H, m), 1.80–1.83(4H, m), 3.68–3.73(4H, m), 6.59(1H, d, J=12 Hz), 6.62(1H, dd, J=6,7 Hz), 7.18(1H, d, J=7 Hz), 7.29–7.37(2H, m), 7.36(1H, d, J=12 Hz), 7.53–7.60(2H, m), 7.80(1H, d, J=8 Hz), 7.87–7.94(1H, m), 8.01–8.07(1H, m), 8.15(1H, dd, J=2,6 Hz).

EXAMPLE 45

(E)-4-[2-(1-naphthyl)vinyl]-2-piperidinopyridine hydrochloride m.p. 209°–211° C.

IR(KBr, cm⁻¹): 3425, 2940, 1640, 1610, 1510, 1280, 1230, 990, 800, 770.

NMR(CD₃OD, δ ppm): 1.74(6H, br s), 3.66(4H, br s), 7.23(1H, d), 7.32(1H, d), 7.40(1H, s), 7.45–7.62(3H, m), 7.74(1H, d), 7.88(3H, d), 8.30(1H, d), 8.39(1H, d).

EXAMPLE 46

(A) (E)-6-methyl-2-[2-(1-naphthyl)vinyl]-4-piperidinopyridine hydrochloride m.p. 234°–236° C.

IR(KBr, cm⁻¹): 3420, 3050, 2935, 2610, 1635, 1620, 1525, 1440, 1355, 1205, 1015, 980, 800.

NMR(CDCl₃, δ ppm): 1.66(6H, s), 2.66(3H, s), 3.43(4H, s), 6.06(1H, d, J=2 Hz), 6.81(1H, d, J=2 Hz), 7.38(1H, d, J=16 Hz), 7.45(1H, dd, J=8,8 Hz), 7.49(1H, dd, J=7,8 Hz), 7.62(1H, dd, J=7,8 Hz), 7.81(2H, dd, J=7,8 Hz), 7.87(1H, d, J=7 Hz), 8.61(1H, d, J=8 Hz), 8.86(1H, d, J=16 Hz).

(B) (Z)-6-methyl-2-[2-(1-naphthyl)vinyl]-4-piperidinopyridine hydrochloride m.p. 205°–207° C.

IR(KBr, cm⁻¹): 3425, 3050, 2930, 2850, 2700, 1620, 1445, 1205, 1015, 840, 820, 790.

NMR(CDCl₃, δ ppm): 1.10–1.60(6H, m), 2.68(3H, s), 2.40–2.90(4H, m), 5.91(1H, d, J=2 Hz), 6.21(1H, d, J=2 Hz), 7.37(1H, d, J=7 Hz), 7.46(1H, t, J=8 Hz), 7.50–7.62(4H, m), 7.80–7.95(3H, m).

EXAMPLE 47

(A) (E)-3-[2-(2-naphthyl)vinyl]-4-piperidinopyridine m.p. 107°–110° C.

IR(KBr, cm⁻¹): 2932, 1584, 1491, 1389, 1242, 981, 933, 816.

NMR(CDCl₃, δ ppm): 1.40–2.00(6H, m), 2.80–3.30(4H, m), 6.70(1H, d, J=5 Hz), 7.15(2H, s), 7.30–8.00(7H, m), 8.24(1H, d, J=5 Hz), 8.57(1H, s).

(B) (Z)-3-[2-(2-naphthyl)vinyl]-4-piperidinopyridine m.p. 80°–83° C.

IR(KBr, cm⁻¹): 2938, 1581, 1488, 1383, 1242, 933, 819.

NMR(CDCl₃, δ ppm): 1.30–1.90(1H, m), 2.90–3.40(4H, m), 6.40(1H, d, J=12 Hz), 6.67(1H, d, J=5 Hz), 6.74(1H, d, J=5 Hz), 7.10–7.80(7H, m), 8.17(1H, d, J=5 Hz), 8.18(1H, s).

EXAMPLE 48

(A) (E)-2-[2-(2-naphthyl)vinyl]-6-piperidinopyridine m.p. 113°–116° C.

IR(KBr, cm⁻¹): 2938, 1587, 1563, 1467, 1449, 1248, 963, 744.

NMR(CDCl₃, δ ppm): 1.30–1.90(6H, m), 3.30–3.80(4H, m), 6.55(1H, d, J=15 Hz), 6.54(1H, s), 6.90–8.00(10H, m).

(B) (Z)-2-[2-(2-naphthyl)vinyl]-6-piperidinopyridine m.p. 89°–92° C.

IR(KBr, cm⁻¹): 2926, 1587, 1563, 1467, 1455, 1278.

NMR(CDCl₃, δ ppm): 1.20–1.80(4H, m), 3.00–3.50(4H, m), 6.40(1H, d, J=12 Hz), 6.43(1H, m), 6.61(1H, s), 6.83(1H, d, J=12 Hz), 7.00–7.90(8H, m).

EXAMPLE 49

(A) (E)-2-[2-(4-biphenylyl)vinyl]-5-methyl-4-piperidinopyridine hydrochloride m.p. 115°–117° C.

IR(KBr, cm⁻¹): 2938, 1644, 1602, 1395, 1125, 762.

NMR(CD₃OD, δ ppm): 1.55(6H, br s), 2.33(3H, s), 3.00–3.50(4H, m), 6.50–7.80(12H, m), 8.02(1H, s).

(B) (Z)-2-[2-(4-biphenylyl)vinyl]-5-methyl-4-piperidinopyridine hydrochloride m.p. 212°–214° C.

IR(KBr, cm⁻¹): 2930, 1580, 1490, 970, 760.

NMR(CD₃OD, δ ppm): 1.70(6H, m), 2.26(3H, s), 3.05(4H, m), 7.10(1H, s), 7.30–7.80(1H, m), 8.16(1H, s).

EXAMPLE 50

(A) (E)-5-methyl-2-(2-phenylvinyl)-4-piperidinopyridine hydrochloride m.p. 170° C. (decomposition)

IR(KBr, cm⁻¹): 2930, 2620, 1600, 1530, 1450, 1240.

NMR(CDCl₃, δ ppm): 1.60(6H, m), 2.30(3H, s), 3.05(4H, m), 6.75(1H, s), 7.20–7.80(7H, m), 8.20(1H, s).

(B) (Z)-5-methyl-2-(2-phenylvinyl)-4-piperidinopyridine hydrochloride m.p. 96°–98° C.

IR(KBr, cm⁻¹): 2950, 1620, 1530, 1450, 1230.

NMR(CDCl₃, δ ppm): 1.75(6H, m), 2.10(3H, s), 3.40(4H, m), 7.20–8.50(9H, m).

EXAMPLE 51

(A) (E)-5-methyl-2-[2-(2-naphthyl)vinyl]-4-piperidinopyridine hydrochloride m.p. 209°–210° C.

IR(KBr, cm⁻¹): 2940, 1590, 1500, 1380, 1230, 980, 970, 820, 750.

NMR(CDCl₃, δ ppm): 1.59(6H, m), 2.15(3H, s) 2.90(4H, m), 6.80(1H, s), 6.95–7.90(9H, m), 8.20(1H, s).

(B) (Z)-5-methyl-2-[2-(2-naphthyl)vinyl]-4-piperidinopyridine hydrochloride m.p. 183°–184° C.

IR(KBr, cm⁻¹): 2930, 1580, 1490, 1440, 1380, 1240, 1120, 760, 540.

NMR(CDCl₃, δ ppm): 1.35(6H, m), 2.10(3H, s), 2.50(4H, m), 6.60(1H, s), 6.61(1H, d, J=12 Hz), 6.90(1H, d, J=12 Hz), 7.20–7.90(7H, m), 8.18(1H, s).

EXAMPLE 52

(A) (E)-5-methyl-2-[2-(6-methyl-2-naphthyl)-vinyl]-4-piperidinopyridine m.p. 108°–110° C.

IR(KBr, cm⁻¹): 2944, 1587, 1491, 1452, 1383, 1230, 972, 870.

NMR(CDCl₃, δ ppm): 1.40–2.00(6H, m), 2.20(3H, s), 2.44(3H, s), 2.70–3.30(4H, m), 6.88(1H, s), 7.00–8.00(8H, m), 8.24(1H, s).

(B) (Z)-5-methyl-2-[2-(6-methyl-2-naphthyl)-vinyl]-4-piperidinopyridine m.p. 90°–92° C.

IR(KBr, cm⁻¹): 2938, 1587, 1491, 1449, 1383, 1242, 897.

NMR(CDCl₃, δ ppm): 1.20–1.80(6H, m), 2.15(3H, s), 2.44(3H, s), 2.30–2.70(4H, m), 6.11(1H, d, J=12 Hz), 6.19(2H, d, J=12 Hz), 7.10–7.80(6H, m), 8.21(1H, s).

EXAMPLE 53

(E)-5-methyl-2-[2-methyl-2-(2-naphthyl)vinyl]-4-piperidinopyridine hydrochloride
m.p. 187°–189° C.
IR(KBr, cm$^{-1}$): 2938, 1587, 1497, 1383, 1224, 816, 750.
NMR(CDCl$_3$, δ ppm): 1.52(6H, m), 2.21(3H, s), 2.68(3H, s), 2.98(4H, m), 6.85(1H, s), 6.90–8.05(8H, m), 8.30(1H, s).

EXAMPLE 54

(Z)-2-[2-(4-biphenylyl)vinyl]-4-methoxy-5-methylpyridine hydrochloride
m.p. 166°–167° C.
IR(KBr, cm$^{-1}$): 3025, 1600, 1570, 1480, 1310, 1260, 1040, 880, 770, 700.
NMR(CDCl$_3$, δ ppm): 2.09(3H, s), 3.45(3H, s), 6.57(1H, d, J=12 Hz), 6.71(1H, s), 6.85(1H, d, J=12 Hz), 7.20–7.80(9H, m), 8.20(1H, s).

EXAMPLE 55

(A) (E)-4-benzyloxy-5-methyl-2-(2-phenylvinyl)pyridine
m.p. 164°–165° C.
IR(KBr, cm$^{-1}$): 3410, 1630, 1480, 1360, 1245, 1165, 760, 700.
NMR(CD$_3$OD, δ ppm): 2.31(3H, s), 5.50(2H, s), 7.26(1H, d, J=16 Hz), 7.35–7.51(6H, m), 7.55(2H, d, J=8 Hz), 7.68–7.75(2H, m), 7.87(1H, s), 7.90(1H, d, J=16 Hz), 8.36(1H, s).

(B) (Z)-4-benzyloxy-5-methyl-2-(2-phenylvinyl)pyridine
m.p. 133°–135° C.
IR(KBr, cm$^{-1}$): 3400, 2630, 1610, 1480, 1320, 1240, 730, 700.
NMR(CD$_3$OD, δ ppm): 2.30(3H, s), 5.10(2H, s), 6.68(1H, d, J=12 Hz), 7.22–7.32(6H, m), 7.32–7.42(6H, m).

EXAMPLE 56

(Z)-2-[2-(2-chlorophenyl)vinyl]-5-methyl-4-piperidinopyridine hydrochloride
m.p. 177°–178° C.
IR(KBr, cm$^{-1}$): 2930, 2370, 1600, 1530, 1440, 1240, 1120, 990, 760.
NMR(CD$_3$OD δ ppm): 1.56(4H, m), 1.66(2H, m), 2.32(3H, s), 3.21(4H, m), 6.64(1H, s), 6.75(1H, d, J=12 Hz), 7.23–7.35(3H, m), 7.40(1H, ddd, J=2, 7, 7, Hz), 7.50(1H, dd, J=1,8 Hz), 8.03(1H, s).

EXAMPLE 57

(A) (E)-2-[2-(2,3-dichlorophenyl)vinyl]-5-methyl-4-piperidinopyridine hydrochloride
m.p. 178°–179° C.
IR(KBr, cm$^{-1}$): 2932, 2806, 1545, 1473, 1416, 1248, 1152, 1113, 1002, 780.
NMR((CD$_3$)$_2$SO, δppm): 1.50–1.70(6H, m), 2.20(3H, s), 2.90–3.04(4H, m), 7.02(1H, s), 7.30–7.95(5H, m), 8.23(1H, s).

(B) (Z)-2-[2-(2,3-dichlorophenyl)vinyl]-5-methyl-4-piperidinopyridine hydrochloride
m.p. 188°–190° C.
IR(KBr, cm$^{-1}$): 2938, 2650, 1626, 1536, 1452, 1383, 1275, 1128, 891, 804.
NMR((CD$_3$)$_2$SO, δppm): 1.36–1.60(6H, m), 2.23(3H, s), 3.10–3.18(4H, m), 6.52(1H, s), 6.90(1H, d, J=12 Hz), 7.20–7.40(3H, m), 7.66(1H, d, J=6 Hz), 8.19(1H, s).

EXAMPLE 58

(A) (E)-2-[2-(2-ethoxycarbonylphenyl)vinyl]-5-methyl-4-piperidinopyridine hydrochloride
m.p. 196°–197° C.
IR(KBr, cm$^{-1}$): 2932, 2608, 1710, 1623, 1479, 1380, 1272, 1239, 969.
NMR(CDCl$_3$, δppm): 1.41(3H, t, J=7 Hz), 1.77(6H, br s), 2.31(3H, s), 3.36(4H, br s), 4.39(2H, q, J=7 Hz), 7.15(1H, s), 7.40–7.50(2H, m), 7.56(1H, m), 7.82(1H, d, J=8 Hz), 8.03(1H, d, J=7 Hz), 8.07(1H, s), 8.52(1H, d, J=16 Hz).

(B) (Z)-2-[2-(2-ethoxycarbonylphenyl)vinyl]-5-methyl-4-piperidinopyridine hydrochloride
m.p. 164°–165° C.
IR(KBr, cm$^{-1}$): 2986, 2848, 2452, 1716, 1620, 1536, 1452, 1368, 1266, 1128, 1017, 870.
NMR(CDCl$_3$, δppm): 1.38(3H, t, J=7 Hz), 1.40–1.60 (6H, m), 2.20(3H, s), 2.80–2.90(4H, m), 4.36(2H, t, J=7 Hz), 6.20(1H, s), 7.08(1H, d, J=12 Hz), 7.19(1H, m), 7.40–7.50(2H, m), 7.54(1H, d, J=12 Hz), 8.00(1H, s), 8.08–8.11(1H, m).

EXAMPLE 59

(A) (E)-3-[2-(1-naphthyl)vinyl]-4-piperidinopyridine
m.p. 124°–127° C.
IR(KBr, cm$^{-1}$): 2938, 1581, 1491, 1383, 1242, 1206, 984, 935, 795, 780.
NMR(CDCl$_3$, δppm): 1.40–2.00(6H, m), 2.80–3.30(4H, m), 6.77(1H, d, J=6 Hz), 7.14(1H, d, J=16 Hz), 7.20–8.30(8H, m), 8.20(1H, s), 8.34(1H, d, J=6 Hz).

(B) (Z)-3-[2-(1-naphthyl)vinyl]-4-piperidinopyridine
m.p. 104°–107° C.
IR(KBr, cm$^{-1}$): 2938, 1584, 1488, 1383, 1245, 930, 780.
NMR(CDCl$_3$, δppm): 1.40–1.90(6H, m), 2.90–3.40(4H, m), 6.64(1H, d, J=12 Hz), 6.66(1H, d, J=6 Hz), 7.00–8.10(8H, m), 7.90(1H, s), 8.09(1H, d, J=6 Hz).

EXAMPLE 60

(E)-3-methyl-2-[2-(1-naphthyl)vinyl]-4-piperidinopyridine
m.p. 133°–135° C.
IR(KBr, cm$^{-1}$): 2930, 1570, 1470, 1250, 800, 775.
NMR(CDCl$_3$, δppm): 1.62(2H, m), 1.74(4H, m), 2.37(3H, s), 3.92(4H, m), 6.78(1H, d), 7.41(1H, d), 7.45–7.56(2H, m), 7.75–7.90(3H, m), 8.33–8.42(3H, m), 8.63(1H, d, J=16 Hz).

EXAMPLE 61

(E)-2-[2-(7-methoxy-1-naphthyl)vinyl]-5-methyl-4-piperidinopyridine
m.p. 173°–175° C.
IR(KBr, cm$^{-1}$): 3004, 2854, 1632, 1542, 1497, 1455, 1257, 1218, 1035, 969, 753
NMR(CDCl$_3$, δppm): 1.40–1.90(6H, m), 2.23(3H, s), 2.80–3.20(4H, m), 3.90(3H, s), 6.82–8.40(10H, m)

EXAMPLE 62

Production of 5-methyl-4-(4-methylpiperidino)-2-[2-(1-naphthyl)ethyl]pyridine hydrochloride:

A suspension of 6.6 g (15.0 mmoles) of (1-naphthylmethyl)triphenylphosphonium chloride in 40 ml of tetrahydrofuran was cooled to about −30° C. in a cooling bath, and under a nitrogen stream, 12.6 ml of 1.55M n-butyllithium in hexane was added dropwise. The reaction mixture was further stirred at the above temperature for 0.5 hour and further a solution of 2.7 g (12.4 mmoles) of 5-methyl-4-(4-methylpiperidino)-2-pyridinecarbaldehyde in 10 ml of tetrahydrofuran was added dropwise. After the addition the cooling bath was removed and the temperature was raised to room temperature. The mixture was further stirred at room temperature for 2 hours. Water (60 ml) was added to the reaction mixture, and tetrahydrofuran was evaporated under-reduced pressure. The remaining aqueous layer was extracted with hexane. The hexane layer was washed with a saturated aqueous sodium chloride solution, dried over anhydrous sodium sulfate, and concentrated under reduced pressure. The resulting oily product was subjected to silica gel column chromatography (eluted with hexane/ethyl acetate=3/1) to give a mixture of (Z)- and (E)-5-methyl-4-(4-methylpiperidino)-2-[2-(1-naphthyl)vinyl]-pyridines as an oil. The mixture of the Z- and E-isomers was dissolved in 30 ml of methanol, and treated with a methanol solution of hydrogen chloride to convert them to hydrochlorides. Then, 100 mg of 10% palladium-carbon was added and the hydrochlorides were hydrogenated at room temperature under atmospheric pressure. After the reaction, the catalyst was remove by filtration. The filtrate was concentrated under reduced pressure. The residue was recrystallized from methanol/ether to give 2.5 g (yield 53%) of the captioned compound as crystals.

m.p. 93°–95° C.

IR(KBr, cm$^{-1}$): 3184, 2944, 2866, 1635, 1506, 1458, 1251, 1134, 978, 804.

NMR(CDCl$_3$, δppm): 0.96(3H, d, J=6 Hz), 0.80–1.40 (2H, m), 1.50–1.70(3H, m), 2.20(3H, s), 2.70(2H, t, J=12 Hz), 3.20–3.50(4H, m), 3.63(2H, s), 5.95(1H, s), 7.20–8.10(8H, m).

EXAMPLES 63–102

In the same way as in Example 62, the following compounds of Examples 63 to 102 were produced.

EXAMPLE 63

5-Methyl-2-[2-(1-naphthyl)ethyl]-4-piperidinopyridine hydrochloride m.p. 67°–68° C.

IR(KBr, cm$^{-1}$): 3420, 2940, 2860, 1640, 1530, 1450, 1240, 801.

NMR(CD$_3$OD, δppm): 1.59(6H, m), 2.19(3H, s), 3.30(4H, m), 3.10–3.70(4H, m), 6.45(1H, s), 7.15–8.20(7H, m).

EXAMPLE 64

2-[2-(2-methoxy-1-naphthyl)ethyl]-5-methyl-4-piperidinopyridine hydrochloride m.p. 170°–171° C.

IR(neat, free base, cm$^{-1}$): 3420, 2940, 2700, 1640, 1530, 1240, 1090, 810, 750.

NMR(CDCl$_3$, free base, δppm): 1.56(6H, m), 2.13(3H, s), 2.87(4H, m), 3.26–3.56(4H, m), 3.86(3H, s), 5.94(1H, s), 7.05–7.50(3H, m), 7.60–7.90(3H, m), 8.00(1H, s).

EXAMPLE 65

5-methyl-2-[2-(4-methyl-1-naphthyl)ethyl]-4-piperidinopyridine hydrochloride m.p. 196°–199° C.

IR(KBr, cm$^{-1}$): 2944, 2518, 1638, 1611, 1530, 1488, 1449, 1242, 762.

NMR(CDCl$_3$, δppm): 1.20–1.80(6H, m), 2.15(3H, s), 2.60(3H, s), 2.80–3.20(4H, m), 3.20–3.80(4H, m), 6.01(1H, s), 7.17(2H, s), 7.30–7.70(2H, m), 7.80–8.30(3H, m).

EXAMPLE 66

2-[2-(4-methoxy-1-naphthyl)ethyl]-5-methyl-4-piperidinopyridine hydrochloride m.p. 167°–168° C.

IR(KBr, cm$^{-1}$): 3442, 2848, 1611, 1527, 1449, 1362, 1275, 1227, 1128, 1005, 819.

NMR(CD$_3$OD, δppm): 1.10–1.90(6H, m), 2.20(3H, s), 2.80–3.60(6H, m), 3.90(3H, s), 6.38(1H, s), 6.60–8.40(14H, m).

EXAMPLE 67

5-methyl-2-[2-(5-methyl-1-naphthyl)ethyl]-4-piperidinopyridine hydrochloride m.p. 90°–93° C.

IR(KBr, cm$^{-1}$): 2938, 1638, 1608, 1533, 1497, 1449, 1242, 798.

NMR(CDCl$_3$, δppm): 1.20–1.80(6H, m), 2.14(3H, s), 2.62(3H, s), 2.80–3.20(4H, m), 3.20–3.80(4H, m), 6.00(1H, s), 7.10–7.60(4H, m), 7.60–8.10(3H, m).

EXAMPLE 68

5-methyl-2-[2-(5-methoxy-1-naphthyl)ethyl]-4-piperidinopyridine hydrochloride m.p. 56°–58° C.

IR(KBr, cm$^{-1}$): 3420, 2940, 1640, 1610, 1585, 1530, 1240, 1040, 1015, 860, 790.

NMR((CD$_3$)$_2$SO, δppm): 1.40–1.80(6H, m), 2.24(3H, s), 3.00–3.70(8H, m), 3.95(3H, s), 6.80–8.30(8H, m).

EXAMPLE 69

5-methyl-2-[2-(7-methoxy-1-naphthyl)ethyl]-4-piperidinopyridine hydrochloride m.p. 166°–167° C.

IR(KBr, cm$^{-1}$): 3442, 2860, 1644, 1533, 1449, 1365, 1245, 1161, 1026, 834.

NMR((CDCl$_3$, δppm): 1.10–1.80(6H, m), 2.15(3H, s), 2.70–3.20(4H, m), 3.20–3.80(4H, m), 3.94(3H, s), 6.00(1H, s), 6.90–8.10(7H, m).

EXAMPLE 70

5-methyl-2-[2-(8-methyl-1-naphthyl)ethyl]-4-piperidinopyridine hydrochloride m.p. 178°–181° C.

IR(KBr, cm$^{-1}$): 2944, 2500, 1638, 1614, 1530, 1482, 1446, 1386, 1242, 1131, 774.

NMR((CDCl$_3$, δppm): 1.30–1.90(6H, m), 2.20(3H), s), 2.88(3H, s), 2.60–3.50(4H, m), 3.50–4.10(4H, m), 5.85(1H, s), 6.90–8.10(7H, m).

EXAMPLE 71

5-methyl-2-[2-(1-naphthyl)ethyl]pyridine hydrochloride m.p. 148°–150° C.

IR(KBr, cm$^{-1}$): 2550, 2380, 2080, 1620, 1560, 1450, 810.

NMR((CD$_3$OD, δppm): 2.40(3H, s), 3.30–3.70(4H, m), 7.20–7.95(7H, m), 7.95–8.55(3H, m).

EXAMPLE 72

4-methoxy-5-methyl-2-[2-(1-naphthyl)ethyl]-pyridine hydrochloride m.p. 170°–173° C.

IR(neat, free base, cm$^{-1}$): 3060, 3020, 2930, 1605, 1575, 1450, 1315, 1245, 1040, 780.

NMR((CDCl$_3$, free base, δppm): 2.11(3H, s), 2.80–3.80(4H, m), 3.65(3H, s), 6.35(1H, s), 7.20–8.20(7H, m), 8.19(1H, s).

EXAMPLE 73

5-methyl-2-[2-(1-naphthyl)ethyl]-4-propoxypyridine hydrochloride
m.p. 164°–166° C.
IR(KBr, cm$^{-1}$): 3500, 3430, 2970, 2875, 1640, 1625, 1485, 1335, 1025, 805, 785.
NMR(CDCl$_3$, δppm): 0.95(3H, t, J=8 Hz), 1.62–1.73 (2H, m), 2.12(3H, s), 3.25–3.31(2H, m), 3.50–3.56(2H, m), 3.72(2H, t, J=7 Hz), 6.24(1H, s), 7.21–7.34(2H, m), 7.42–7.49(2H, m), 7.68(1H, d, J=8 Hz), 7.81(1H, dd, J=2,8 Hz), 8.04(1H, d, J=8 Hz), 8.20(1H, s).

EXAMPLE 74

4-isopentyloxy-5-methyl-2-[2-(1-naphthyl)ethyl]-pyridine hydrochloride
m.p. 70°–71° C.
IR(KBr, cm$^{-1}$): 3515, 3450, 2960, 2870, 1645, 1625, 1490, 1340, 1240, 1165, 800, 785.
NMR(CDCl$_3$, δppm): 0.94(6H, d, J=7 Hz), 1.63(2H, q, J=7 Hz), 1.70–1.81(1H, m), 2.15(3H, s), 3.25–3.31(2H, m), 3.52–3.59(2H, m), 3.83(2H, t, J=7 Hz), 6.30(1H, s), 7.25–7.40(2H, m), 7.45–7.54(2H, m), 7.72(1H, d J=8 Hz), 7.86(1H, dd, J=2,8 Hz), 8.10(1H, dd, J=1,8 Hz), 8.23(1H, s).

EXAMPLE 75

5-methyl-2-[2-(1-naphthyl)ethyl]-4-pentyloxypyridine hydrochloride
m.p. 75°–76° C.
IR(KBr, cm$^{-1}$): 3500, 2950, 1640, 1490, 1340, 1240, 1165, 800.
NMR(CD$_3$OD, δppm): 0.95(3H, t, J=4 Hz), 1.42(4H, m), 1.80(2H, m), 2.25(3H, s), 3.35(2H, t, J=8 Hz), 3.58(2H, t, J=7 Hz), 4.10(2H, t, J=7 Hz), 7.26(1H, d, J=7 Hz), 7.37(1H, dd, J=8,8 Hz), 7.46–7.58(2H, m), 7.77(1H, d, J=8 Hz), 7.88(1H, dd, J=2,8 Hz), 8.09(1H, d, J=8 Hz), 8.26(1H, s).

EXAMPLE 76

4-cyclohexyloxy-5-methyl-2-[2-(1-naphthyl)-ethyl]-pyridine hydrochloride
m.p. 182°–184° C.
IR(KBr, cm$^{-1}$): 2932, 1638, 1620, 1482, 1335, 1242, 1164.
NMR(CD$_3$OD, δppm): 1.25–1.63(6H, m), 1.63–1.80(4H, m), 2.18(3H, s), 3.38(2H, t, J=7 Hz), 3.57(2H, t, J=7 Hz), 4.40–4.52(1H, m), 6.89(1H, s), 7.22(1H, d, J=7 Hz), 7.35(1H, dd, J=7,8 Hz), 7.49(1H, dt, J=2,7 Hz), 7.53(1H, dt, J=2,7 Hz), 7.76(1H, d, J=8 Hz), 7.87(1H, dd, J=2,7 Hz), 8.03(1H, dd, J=2,7 Hz), 8.27(1H, s).

EXAMPLE 77

5-methyl-2-[2-(1-naphthyl)ethyl]-4-phenoxypyridine
m.p. 60°–62° C.
IR(KBr, cm$^{-1}$): 1599, 1566, 1491, 1287, 1206, 798, 786.
NMR(CDCl$_3$, δppm): 2.28(3H, s), 3.07(2H, dd, J=7,9 Hz), 3.43(2H, dd, J=7,9 Hz), 6.27(1H, s), 6.82–6.88(2H, m), 7.16(1H, tt, J=1,8 Hz), 7.23(1H, dd, J=2,7 Hz), 7.29–7.38(3H, m), 7.42–7.49(2H, m), 7.71(1H, d, J=8 Hz), 7.81–7.88(1H, m), 7.97–8.04(1H, m), 8.39(1H, s).

EXAMPLE 78

5-methyl-2-[2-(1-naphthyl)ethyl]-4-phenethyloxypyridine hydrochloride
m.p. 171°–172° C.
IR(KBr, cm$^{-1}$): 3045, 2925, 2860, 1640, 1485, 1475, 1320, 1030, 1015, 875, 775.
NMR(CDCl$_3$, δppm): 2.13(3H, s), 2.98(2H, t, J=6 Hz), 3.48(2H, t, J=7 Hz), 3.63(2H, t, J=7 Hz), 3.94(2H, t, J=6 Hz), 6.15(1H, s), 7.12–7.15(2H, m), 7.20–7.36(5H, m), 7.42–7.54(2H, m), 7.67(1H, d, J=8 Hz), 7.79(1H, d, J=8 Hz), 8.03(1H, d, J=Hz), 8.21(1H, s).

EXAMPLE 79

4-dimethylamino-5-methyl-2-[2-(1-naphthyl)-ethyl]-pyridine hydrochloride
m.p. 196°–199° C.
IR(KBr, cm$^{-1}$): 2878, 2758, 1644, 1608, 1545.
NMR(CDCl$_3$, δppm): 2.20(3H, s), 2.88(6H, s), 3.10–3.70(4H, m), 6.03(1H, s), 7.20–8.20(8H, m).

EXAMPLE 80

5-methyl-2-[2-(1-naphthyl)ethyl]-4-(pyrrolidin-1-yl)pyridine hydrochloride
m.p. 205°–208° C.
IR(KBr, cm$^{-1}$): 2644, 1644, 1608, 1539, 1509, 1485, 1458.
NMR(CDCl$_3$, δppm): 1.70–2.10(4H, m), 2.29(3H, s), 3.00–3.80(8H, m), 5.90(1H, s), 7.30–8.30(8H, m).

EXAMPLE 81

5-methyl-4-morpholino-2-[2-(1-naphthyl)ethyl]pyridine hydrochloride
m.p. 215°–217° C.
IR(KBr, cm$^{-1}$): 2860, 2728, 1641, 1611, 1536, 1485, 1440, 1240, 1113.
NMR(CDCl$_3$, δppm): 2.12(3H, s), 2.80–3.20(4H, m), 3.20–3.90(8H, m), 6.20(1H, s), 7.10–8.20(8H, m).

EXAMPLE 82

5-methyl-4-(4-methyl-piperazin-1-yl)-2-[2-(1-naphthyl)ethyl]pyridine hydrochloride
m.p. 150° C. (decomposition)
IR(KBr, cm$^{-1}$): 3436, 2908, 2692, 1638, 1611, 1533, 1491, 1455, 1242.
NMR(CD$_3$OD, δppm): 2.32(3H, s), 2.95(3H, s), 3.10–3.90(12H, m), 6.92(1H, s), 7.30–8.10(7H, m), 8.15(1H, s).

EXAMPLE 83

5-methyl-2-[2-(1-naphthyl)ethyl]-4-(perhydroazepin-1-yl)pyridine hydrochloride
m.p. 81°–83° C.
IR(KBr, cm$^{-1}$): 3502, 2926, 1644, 1536, 1503, 1452.
NMR(CD$_3$OD, δppm): 1.30–1.40(4H, m), 1.40–1.50(4H, m), 2.38(3H, s), 3.22(2H, t, J=7 Hz), 3.52(2H, t, J=7 Hz), 3.50–3.60(4H, m), 6.23(1H, s), 7.21(1H, d, J=7 Hz), 7.34(1H, dd, J=7,8 Hz).

EXAMPLE 84

5-methyl-4-(3-methylpiperidino)-2-[2-(1-naphthyl)ethyl]pyridine hydrochloride
m.p. 76°–78° C.
IR(KBr, cm$^{-1}$): 2926, 1638, 1608, 1530, 1497, 1446, 1242.
NMR(CD$_3$OD, δppm): 0.87(3H, d, J=7 Hz), 1.08–1.24(1H, m), 1.24–1.52(2H, m), 1.62–1.75(1H, m), 1.82(1H, dd, J=4,13 Hz), 2.27(3H, s), 2.56(1H, dd, J=11,13 Hz), 2.88(1H, dt, J=3,13 Hz), 3.20–3.30(2H, m), 3.35–3.63(4H, m), 6.43(1H, s), 7.24(1H, d, J=7 Hz), 7.36(1H, dd, J=7,8 Hz), 7.45–7.55(2H, m), 7.76(1H, d, J=8 Hz), 7.97(1H, s), 7.83–7.93(1H, m), 8.01(1H, dd, J=2,6 Hz).

EXAMPLE 85

4-diethylamino-5-methyl-2-[2-(1-naphthyl)ethyl]pyridine hydrochloride m.p. 108°–111° C.

IR(KBr, cm$^{-1}$): 2752, 1641, 1602, 1536, 1488, 1245.

NMR(CD$_3$OD, δppm): 1.04(3H, t, J=7 Hz), 2.36(3H, s), 3.21(2H, t, J=7 Hz), 3.43(2H, q, J=7 Hz), 3.52(2H, t, J=7 Hz), 6.36(1H, s), 7.24(1H, dd, J=1,7 Hz), 7.35(1H, dd, J=7,8 Hz), 7.47(1H, dt, J=2,6 Hz), 7.52(1H, dt, J=2,7 Hz), 7.74(1H, d, J=8 Hz), 7.85(1H, s), 7.84–7.89(1H, m), 8.01–8.06(1H, m).

EXAMPLE 86

2-[2-(1-naphthyl)ethyl]-4-piperidinopyridine hydrochloride m.p. 204°–206° C.

IR(KBr, cm$^{-1}$): 2930, 2780, 1640, 1540, 1250, 800, 780.

NMR(CD$_3$OD, δppm): 1.60(6H, br s), 2.90–3.80(8H, m), 6.55(1H, s), 6.85(1H, d, J=6 Hz), 7.15–8.20(8H, m).

EXAMPLE 87

5-ethyl-2-[2-(1-naphthyl)ethyl]-4-piperidinopyridine hydrochloride m.p. 73°–74° C.

IR(KBr, cm$^{-1}$): 3455, 3400, 2940, 1640, 1610, 1500, 1240, 1125, 805, 780.

NMR(CDCl$_3$, δppm): 1.20(3H, t, J=8 Hz), 1.30–1.80 (6H, m), 2.50(2H, q, J=8 Hz), 2.70–3.20(4H, m), 3.10–3.80(4H, m), 6.05(1H, s), 7.20–8.10(8H, m).

EXAMPLE 88

2-[2-(1-naphthyl)ethyl]-4-piperidino-5-propylpyridine hydrochloride m.p. 135°–138° C. (decomposition)

IR(KBr, cm$^{-1}$): 3450, 2930, 2650, 1640, 1610, 1470, 1390, 1240, 780.

NMR(CDCl$_3$, δppm): 0.92(3H, t, J=6 Hz), 1.40–1.80 (6H, m), 2.10–2.70(2H, m), 2.91(4H, br s), 3.20–3.80(4H, m), 7.10–8.20(9H, m).

EXAMPLE 89

3-[2-(1-naphthyl)ethyl]-2-piperidinopyridine hydrochloride m.p. 155°–157° C.

IR(KBr, cm$^{-1}$): 3450, 3070, 2930, 2850, 1605, 1455, 1250, 800, 770.

NMR(CDCl$_3$, δppm): 1.59(5H, s), 3.12(2H, t, J=8 Hz) 3.30(4H, s), 3.42(2H, t, J=8 Hz), 7.05–7.20(2H, m), 7.34(1H, dd, J=7, 8 Hz), 7.48–7.58(2H, m), 7.72–7.79(2H, m), 7.86–7.90(1H, m), 8.03(1H, dd, J=2, 8 Hz), 8.31(1H, d, J=5 Hz).

EXAMPLE 90

4-[2-(1-naphthyl)ethyl]-2-piperidinopyridine hydrochloride m.p. 138°–139° C.

IR(KBr, cm$^{-1}$): 3500, 2940, 2750, 1650, 1610, 1450, 1230, 800, 780.

NMR(CD$_3$OD, δppm): 1.65(4H, m), 1.76(2H, m), 3.15 (2H, t, J=2 Hz), 3.46(2H, t, J=8 Hz), 3.54(4H, m), 6.83(1H, dd, J=1, 6 Hz), 6.89(1H, s), 7.28(1H, d, J=6 Hz), 7.37(1H, dd, J=8, 8 Hz), 7.44–7.56(2H, m), 7.74(2H, d, J=6 Hz), 7.86(1H, dd, J=2, 8 Hz), 8.07(1H, dd, J=8 Hz).

EXAMPLE 91

6-methyl-2-[2-(1-naphthyl)ethyl]-4-piperidinopyridine hydrochloride m.p. 220°–222° C.

IR(KBr, cm$^{-1}$): 3050, 2930, 1640, 1540, 1385, 1215, 1020, 805, 785.

NMR(CDCl$_3$, δppm): 1.40–1.80(6H, m), 2.73(3H, s), 3.28(4H, t, J=5 Hz), 3.38(2H, t, J=7 Hz), 3.66(2H, t, J=7 Hz), 5.80(1H, d, J=3 Hz), 6.30(1H, d, J=3 Hz), 7.32–7.56(4H, m), 7.64–7.72(1H, m), 7.83(1H, d, J=1, 8 Hz), 8.08(1H, dd, J=1, 8 Hz).

EXAMPLE 92

3-[2-(2-naphthyl)ethyl]-4-piperidinopyridine hydrochloride m.p. 171°–174° C.

IR(KBr, cm$^{-1}$): 2932, 1638, 1509, 1449, 1254, 852, 807.

NMR(CDCl$_3$, δppm): 1.40–2.00(6H, m), 3.02(4H, s), 3.10–3.60(4H, m), 7.01(1H, d, J=6 Hz), 7.10–7.90(7H, m), 8.21(1H, d, J=6 Hz), 8.27(1H, s).

EXAMPLE 93

2-[2-(2-naphthyl)ethyl]-6-piperidinopyridine m.p. 49°–51° C.

IR(KBr, cm$^{-1}$): 2932, 1590, 1467, 1248.

NMR(CDCl$_3$, δppm): 1.30–1.90(6H, m), 2.80–3.30(4H, m), 6.33(1H, br s), 6.47(1H, d, J=3 Hz), 7.20–8.00(8H, m).

EXAMPLE 94

2-[2-(4-biphenyl)ethyl]-5-methyl-4-piperidinopyridine hydrochloride m.p. 191°–193° C.

IR(KBr, cm$^{-1}$): 2940, 1640, 1610, 1530, 1490, 1410, 1246, 760, 700.

NMR(CD$_3$OD, δppm): 1.60(6H, m), 2.25(3H, s), 3.10 (4H, m), 3.20–3.50(4H, m), 6.68(1H, s), 7.10–7.70(9H, m), 7.95(1H, s).

EXAMPLE 95

5-methyl-2-phenethyl-4-piperidinopyridine hydrochloride m.p. 160°–161° C.

IR(KBr, cm$^{-1}$): 2930, 1600, 1500, 1460, 700.

NMR(CDCl$_3$, δppm): 1.52(6H, m), 2.10(3H, s), 2.78(4H, m), 2.90(4H, s), 6.41(1H, s), 7.10(5H, s), 8.10(1H, s).

EXAMPLE 96

5-methyl-2-[2-(2-naphthyl)ethyl]-4-piperidinopyridine hydrochloride m.p. 134°–135° C.

IR(KBr, cm$^{-1}$): 3400, 2930, 1640, 1540, 1450, 1250.

NMR(CD$_3$OD, δppm): 1.50(6H, m), 2.20(3H, s), 3.10–3.40(8H, m), 6.58(1H, s), 7.20–8.00(8H, m).

EXAMPLE 97

5-methyl-2-[2-(6-methyl-2-naphthyl)ethyl]-4-piperidinopyridine hydrochloride m.p. 79°–82° C.

IR(KBr, cm$^{-1}$): 2936, 1640, 1612, 1530, 1496, 1448, 1242.

NMR(CDCl$_3$, δppm): 1.20–1.80(6H, m), 2.14(3H, s), 2.43(3H, s), 2.80–3.50(4H, m), 3.28(4H, s), 6.25(1H, s), 7.00–7.80(6H, m), 7.93(1H, s).

EXAMPLE 98

5-methyl-2-[2-methyl-2-(2-naphthyl)ethyl]-4-piperidinopyridine hydrochloride

Caramel-like

IR(neat, cm$^{-1}$): 2950, 2860, 1640, 1530, 1500, 1450, 1240, 690.

NMR (CD$_3$OD, δppm): 1.10(3H, d, J=7 Hz), 1.20–1.60(6H, m), 2.19(3H, s), 3.10(7H, m), 6.30(1H, s), 7.20–8.00(8H, m).

EXAMPLE 99

2-[2-(4-biphenylyl)ethyl]-4-methoxy-5-methylpyridine m.p. 56°–58° C.

IR(KBr, cm$^{-1}$): 2940, 2860, 1630, 1535, 1510, 1350, 1235, 770.

NMR(CDCl$_3$, δppm): 2.15(3H, s), 3.18(4H, s), 3.80(3H, s), 6.51(1H, s), 7.25–7.62(9H, m), 8.20(1H, s).

EXAMPLE 100

2-[(2-ethoxycarbonylphenyl)ethyl]-5-methyl-4-piperidinopyridine hydrochloride m.p. 112°–114° C.

IR(KBr, cm$^{-1}$): 2938, 2752, 1644, 1533, 1446, 1284, 1242, 1020.

NMR(CDCl$_3$, δppm): 1.40(3H, t, J=7 Hz), 1.71(6H, s), 2.27(3H, s), 3.20–3.40(6H, m), 3.40–3.50(4H, m), 4.35(2H, q, J=7 Hz), 6.65(1H, s), 7.20–7.50 (3H, m), 7.92(1H, d, J=8 Hz), 8.05(1H, s).

EXAMPLE 101

3-[2-(1-naphthyl)ethyl]-4-piperidinopyridine hydrochloride m.p. 180°–183° C.

IR(KBr, cm$^{-1}$): 2930, 2536, 1638, 1515, 1485, 1455, 1386, 1263, 777.

NMR(CDDl$_3$, δppm): 1.30–1.80(6H, m), 2.80–3.50 (8H, m), 6.80–8.40(10H, m).

EXAMPLE 102

3-methyl-2-[2-(1-naphthyl)ethyl]-4-piperidinopyridine hydrochloride m.p. 154°–155° C.

IR(KBr, cm$^{-1}$): 2940, 2550, 1625, 1488, 1377, 1254, 780.

NMR(CDCl$_3$, δppm): 1.61(4H, s), 1.63(3H, s), 1.80(2H, br s), 2.98(4H, br s), 3.47(2H, t), 3.65(2H, t), 6.85(1H, br s), 7.29–7.40(2H, m), 7.40–7.52(2H, m), 7.70(1H, d), 7.81(1H, d), 8.05(1H, d), 8.23(1H, br s).

EXAMPLE 103

Production of 2-[2-[4-fluoro-1-naphthyl)ethyl]-5-methyl-4-piperidinopyridine hydrochloride:

Platinum oxide (5 mg) was added to a solution of 43 mg of (E)-2-[2-(4-fluoro-1-naphthyl)vinyl]-5-methyl-4-piperidinopyridine hydrochloride in 4 ml of methanol, and hydrogenation was carried out at room temperature under atmospheric pressure. After the reaction, the catalyst was removed by filtration. The filtrate was concentrated under reduced pressure, and recrystalized from methanol/ether to give 38 mg (yield 95%) of the captioned compound.

m.p. 115°–117° C.

IR(KBr, cm$^{-1}$): 3496, 2938, 1638, 1608, 1533, 1497, 1467, 1395, 852.

NMR((CD$_3$)$_2$SO, δppm): 1.63(4H, s), 2.30(3H, s), 3.43(4H, s), 3.80–5.00(2H, br s), 5.30(2H, s), 6.80–7.50(6H, m), 8.20(1H, s).

EXAMPLES 104–107

In the same way as in Example 103, the following compounds of Examples 104 to 107 were produced.

EXAMPLE 104

2-[2-(4-Chloro-1-naphthyl)ethyl]-5-methyl-4-piperidinopyridine hydrochloride m.p. 199°–201° C.

IR(KBr, cm$^{-1}$): 2944, 2524, 1638, 1611, 1530, 1491, 1449, 1224.

NMR(CDCl$_3$, δppm): 1.20–1.80(6H, m), 2.13(3H, s), 2.80–3.20(4H, m), 3.20–3.80(4H, m), 6.11(1H, s), 7.10–7.80(4H, m), 7.80–8.40(3H, m).

EXAMPLE 105

2-[2-(2-chlorophenyl)ethyl]-5-methyl-4-piperidinopyridine hydrochloride m.p. 155°–156° C.

IR(KBr, cm$^{-1}$): 3050, 2765, 1600, 1450, 1413, 1275, 1150, 1127, 890, 750.

NMR(CD$_3$OD, δppm): 1.67(6H, m), 2.32(3H, s), 3.14–3.19(4H, m), 3.30(4H, m), 6.70(1H, s), 7.21–7.26(3H, m), 7.34(1H, m), 7.99(1H, s).

EXAMPLE 106

2-[2-(2,3-dichlorophenyl)ethyl]-5-methyl-4-piperidinopyridine hydrochloride m.p. 190°–191° C.

IR(KBr, cm$^{-1}$): 2938, 2680, 1638, 1533, 1455, 1383, 1305, 1242, 1164, 1050, 861, 807.

NMR(CDCl$_3$, δppm): 1.71(6H, s), 2.28(3H, s), 3.10–3.40(8H, m), 6.42(1H, s), 7.08–7.40(3H, m), 8.03(1H, s).

EXAMPLE 107

4-benzyloxy-5-methyl-2-[2-(1-naphthyl)ethyl]-pyridine hydrochloride m.p. 84°–86° C.

IR(KBr, cm$^{-1}$): 3262, 2656, 1641, 1485, 1458, 1341, 1245, 1167, 732.

NMR(CD$_3$OD, δppm): 2.25(3H, s), 3.37(2H, t, J=7 Hz), 3.56(2H, t, J=7 H), 5.28(2H, s), 7.19(1H, d, J=7 Hz), 7.31(1H, s), 7.35(1H, dd, J=7, 8 Hz), 7.37–7.46(5H, m), 7.46–7.58(2H, m), 7.71(1H, d, J=8 Hz), 7.89(1H, dd, J=2, 8 Hz), 8.07(1H, d, J=8 Hz), 8.27(1H, d, J=1 Hz).

EXAMPLE 108

Production of 5-methyl-2-[3-(1-naphthyl)-3-oxo-1-propenyl]-4-piperidinopyridine hydrochloride:

A 10% aqueous solution of sodium hydroxide (1.6 ml) and then 174 mg of 1-acetylnaphthalene at about 4° C. were added to a solution of 204 mg (1.0 mmole) of 5-methyl-4-piperidino-2-pyridinecarbaldehyde in 3 ml of methanol, and the mixture was allowd to stand overnight at the above temperature. The reaction mixture was concentrated under reduced pressure. The residue was mixed with water, and then extracted with dichloromethane. The dichloromethane layer was dried over anhydrous sodium sulfate, and concentrated under reduced pressure. The residue was purified by silica gel column chromatography (eluted with dichloromethane) to give 5-methyl-2-[3-(1-naphthyl)-3-oxo-1- propenyl]-4-piperidinopyridine. The product was treated with an ethanol solution of hydrogen chloride to form its hydrochloride. Recrystallization from methanol/ether gave 350 mg (yield 75%) of the captioned compound as crystals.

m.p. 201°–204° C.

IR(KBr, cm$^{-1}$): 2940, 1680, 1640, 1600, 1540, 1450, 1318, 1260, 1110, 790.

NMR(CDCl$_3$, δppm): 1.73(6H, m), 2.26(3H, s), 3.45(4H, m), 7.10–8.70(11H, m).

EXAMPLE 109

Production of 2-[3-hydroxy-3-(1-naphthyl)-propyl]-5-methyl-4-piperidinopyridine:

A solution of 759 mg (2.12 mmoles) of 5-methyl-2-[3-(1-naphthyl)-3-oxo-2-propenyl]-4-piperidinopyridine in 2 ml of ether was added dropwise to a suspension of 83 mg (2.18 mmoles) of lithium aluminum hydride in 3 ml of ether, and the mixture was heated under reflux for 1 hour.

Water-saturated ether was added to decompose the excess of the reducing agent, and 1 ml of water was further added. The ether layer was separated and dried over anhydrous sodium sulfate. The solvent was evaporated under reduced pressure. The residue was purified by silica gel column chromatography [eluted with chloroform/ethyl acetate(=3/1) and then with chloroform/methanol (=20/1)] to give 618 mg (yield 81%) of the captioned compound.

Oil

IR(neat, cm$^{-1}$): 3200, 2930, 1600, 1500, 1380, 1240, 1040, 780.

NMR(CDCl$_3$, δppm): 1.55(6H, m), 2.00–2.35(5H, m), 2.65–3.05(6H, m), 5.25(1H, br s), 5.52(1H, t, J=4 Hz), 6.52(1H, s), 7.20–8.15(8H, m).

EXAMPLE 110

Production of 5-methyl-2-[3-(1-naphthyl)-3-oxopropyl]-4-piperidinopyridine:

Manganese dioxide (660 mg) was added to a solution of 200 mg of 2-[3-hydroxy-3-(1-naphthyl)-propyl]-5-methyl-4-piperidinopyridine in 10 ml of chloroform, and the mixture was stirred overnight at room temperature. The reaction mixture was filtered, and the filtrate was concentrated under reduced pressure. The residue was purified by silica gel column chromatography [eluted with chloroform and then with chloroform/methanol (=50/1)] to give 150 mg (yield 75%) of the captioned compound.

Oil

IR(CHCl$_3$, cm$^{-1}$): 2950, 1690, 1640, 1530, 1450, 1240, 670.

NMR(CDCl$_3$, δppm): 1.59(6H, m), 2.12(3H, s), 2.87(4H, m), 3.00–3.65(4H, m), 6.76(1H, s), 7.25–8.65(9H, m).

EXAMPLE 111

Production of 5-methyl-2-[3-(1-naphthyl)propyl]-4-piperidinopyridine hydrochloride:

To a solution of 86 mg of 5-methyl-2-[3-(1-naphthyl)-3-oxopropyl]-4-piperidinopyridine in 2 ml of triethylene glycol was added 48 mg of 100% hydrazine hydrate, and the mixture was heated at 110° to 120° C. for 2 hours. Then, 68 mg of potassium hydroxide was added, and the bath temperature was raised to about 185° C. The mixture was further heated at this temperature for 5 hours. The reaction mixture was poured into ice and extracted with ether. The ether layer was washed with water, dried over anhydrous sodium sulfate, and concentrated under reduced pressure. The residue was purified by silica gel column chromatography (eluted with chloroform) to give 5-methyl-2-[3-(1-naphthyl)-propyl]-4-piperidinopyridine as an oil. The product was treated witn an ethanol solution of hydrogen chloride, and recrystallized from acetone/ether to give 28 mg (yield 28%) of the captioned compound.

m.p. 126°–128° C.

IR(KBr, cm$^{-1}$): 2930, 1640, 1530, 1490, 1230, 780.

NMR(CD$_3$OD, δppm): 1.70(6H, m), 2.23(5H, m), 2.84(2H, t), 3.23(2H, t), 6.80(1H, s), 7.30–7.83(7H, m), 8.03(1H, d).

EXAMPLE 112

Production of 2-[alpha-hydroxy-(1-naphthyl)-methyl]-5-methyl-4-piperidinopyridine:

A Grignard reagent prepared from 243 mg (10 moles) of magnesium and 1.4 ml of 1-bromonaphthalene was gradually added dropwise at room temperature to a solution of 204 mg of 5-methyl-4-piperidino-2-pyridinecarbaldehyde in 5 ml of benzene. When the starting aldehyde was consumed, the addition of the Grignard reagent was stopped. A saturated aqueous ammonium chloride solution was added, and the mixture was stirred for 30 minutes and made alkaline by adding sodium carbonate. The organic layer was then separated, dried over anhydrous sodium sulfate, and then concentrated under reduced pressure. The residue was purified by silica gel column chromatography [eluted with benzene/ethyl acetate(=10/1) and then with benzene/ethyl acetate (=5/1)] to give 220 mg (yield 66%) of the captioned compound Oil IR(neat, cm$^{-1}$): 3300, 2940, 1600, 1380, 1220, 1040, 790.

NMR(CDCl$_3$, δ ppm): 1.45(6H, m), 2.10(3H, s), 2.68(4H, m), 4.50(1H, br s), 6.27(1H, s), 6.48(1H, s), 7.20–8.30(8H, m).

EXAMPLE 113

Production of 5-methyl-2-(1-naphthoyl)-4-piperidinopyridine:

Manganese dioxide (3.5 g) was added to a solution of 141 mg (0.42 mmole) of 2-[alpha-hydroxy-(1-naphthyl)-methyl]-5-methyl-4-piperidinopyridine in a 5 ml of-dichloromethane, and the mixture was stirred overnight. The reaction mixture was filtered, and the filtrate was concentrated under reduced pressure. The residue was purified by silica gel column chromatography (eluted with chloroform) to give 98 mg (71%) of the captioned compound.

Oil

IR(neat, cm$^{-1}$): 2930, 1670, 1580, 1250, 910, 790.

NMR(CDCl$_3$, δ ppm): 1.63(6H, m), 2.25(2H, s), 3.00(4H, m), 7.20–8.40(9H, m).

EXAMPLE 114

Production of 5-methyl-2-(1-naphthylmethyl)-4-piperidinopyridine hydrochloride:

To a solution of 5-methyl-2-(1-napthoyl)-4-piperidinopyridine in 1 ml of triethylene glycol was added 30 mg of 100% hydrazine hydrate, and the mixture was stirred at 120° C. for 1.5 hours. Potassium hydroxide (42 mg) was added to the reaction mixture, and the mixture was heated at about 200° C. for 1 hour. The reaction mixture was poured into water, and extracted with ether. The ether layer was washed with water, dried and concentrated under reduced pressure. The residue was purified by silica gel column chromatography [eluted with chloroform and then with chloroform/methanol (=50/1)] to give 5-methyl-2-(1-naphthylmethyl)-2-piperidinopyridine as an oil. The oil was treated with an ethanol solution of hydrogen chloride and recrystallized from acetone/ether to give 44 mg (yield 40%) of the captioned compound.

m.p. 186°-189° C.

IR(KBr, cm$^{-1}$): 2930, 1590, 1500, 1400, 1240, 1040, 780.

NMR(CD$_3$OD, δ ppm): 1.50(6H, m), 2.10(3H, s), 2.70(4H, m), 4.50(2H, s), 6.46(1H, s), 7.20–8.10(7H, m), 8.15(1H, s).

FORMULATION EXAMPLE 1

Two hundred grams of (Z)-5-methyl-2-[2-(1-naphthyl)vinyl]-4-piperidinopyridine hydrochloride was mixed with 70.3 g of lactose, 67.9 g of potato starch and 12.8 g of colloidal silica. A moderate amount of a 10% aqueous solution of gelatin was added to the mixture to wet it, and the mixture was pulverized through a 12-mesh sieve. After drying, 64 g of potato starch, 20 g of talc and 2 g of magnesium stearate were added. The resulting mixture was compressed to produce 4,000 tablets each containing 50 mg of the active compound of the invention.

FORMULATION EXAMPLE 2

Two hundred grams of (Z)-5-methyl-2-[2-(1-naphthyl)ethyl]-4-piperidinopyridine was mixed with an alcohol solution of 70.3 g of lactose and 10 g of polyvinyl pyrrolidone, and granulated. After drying, the granules were mixed with 10 g of talc, 16 g of potato starch and 1 g of magnesium stearate and then compressed into 4,000 tablets. The tablets were each coated with a 10% alcohol solution of shellac, and then further coated with an aqueous solution containing 45% sucrose, 5% gun arabic, 4% gelatin and 0.2% dye. This coating was repeated five times further, and then talc and powdery sugar were used for subcoating. The coated tablets were further coated with a syrup containing 66% sugar and lustered with a 10% carnauba wax solution in carbon tetrachloride.

FORMULATION EXAMPLE 3

A syrup containing 2% (w/v) of an active compound of the invention was prepared from the following ingredients.

(Z)-5-methyl-2-[2-(1-naphthyl)vinyl]-4-piperidino pyridine hydrochloride: 2.0 g
Saccharin: 0.6 g
Sugar: 30.0 g
Glycerin: 5.0 g
Seasoning: 0.1 g
96% ethanol: 10.1 ml
Distilled water (in an amount required to adjust the final volume to 100 ml)

Sugar, saccharin and the above acid addition salt were dissolved in 60 g of warm water. After cooling, glycerin and a solution of the seasoning in ethanol were added. Water was added to the mixture to adjust its final volume to 100 ml.

The above active compound may be replaced by other pharmaceutically acceptable acid addition salts provided by this invention.

FORMULATION EXAMPLE 4

Ten grams of (Z)-5-methyl-2-[2-(1-naphthyl)-ethyl]-4-piperidinopyridine hydrochloride, 6 g of sodium chloride and 1 g of ascorbic acid were dissolved in a sufficient amount of distilled water to preprare 1000 ml of a solution. This solution contained 10 mg of the active compound per ml. The solution was filled in ampoules and sterilized by heating at 120° C. for 20 minutes.

What is claimed is:

1. A substituted pyridine derivative of the formula (I)

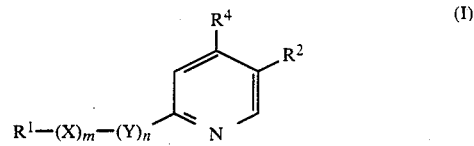

wherein $R^1$-$(X)_m$ represents a phenyl, phenoxy, phenylthio, 4-biphenylyl, 4-biphenyloxy, naphthyl or napththylthio group and wherein said groups are unsubstituted or substituted by one or two substituents selected from the group consisting of $C_{1-4}$ alkyl, $C_{1-4}$ alkoxy, $C_{5-8}$ cycloalkyl, and halogen atoms; Y represents methylene, ethylene or vinylene, n is 1, $R^2$ represents hydrogen or $C_{1-4}$ alkyl; and $R^4$ represents a $C_{1-4}$ alkyloxy, benzyloxy, diethylamino, cyclohexyloxy, piperidino or perhydroazepin-1-yl group, which groups are unsubstituted or substituted by a $C_{1-4}$ alkyl; or an acid addition salt thereof.

2. The compound of claim 1 which is selected from the group consisting of (Z)-5-methyl-2-[2-(1-naphthyl)-vinyl]-4-piperidinopyridine, 5-methyl-2-[2-(1-naphthyl)-ethyl]-4-piperidinopyridine, (Z)-5-methyl-2-[2-(1-naphthyl)vinyl]-4-(perhydroazepin-1-yl)pyridine, 5-methyl-2-[2-(1-naphthyl)ethyl]-4-(perhydroazepin-1-yl)-pyridine, (Z)-5methyl-4-(4-methylpiperidino)-2-[2-(1-naphthyl)vinyl]pyridine, 5-methyl-4-(4-methylpiperidino)-2-[2-(1-naphthyl)ethyl]pyridine, (Z)-5-methyl-4-(3-methylpiperidino)-2-[2-(1-naphthyl)vinyl]-pyridine, 5-methyl-4-(3-methylpiperidino)-2-[2-(1-naphthyl)ethyl]-pyridine, (Z)-5-ethyl-[2-(1-naphthyl)vinyl]-4-piperidinopyridine, (Z)-4-cyclohexyloxy-5-methyl-2-[2-(1-naphthyl)vinyl]pyridine, 4-cyclohexyloxy-5-methyl-2-[2-(1-naphthyl)ethyl]pyridine, (Z)-5-methyl-2-[2-(4-methyl-1-naphthyl)vinyl]-4-piperidinopyridine, 5-methyl-2-[2-(4-methyl-1-naphthyl)ethyl]-4-piperidinopyridine, (Z)-2-[2-(4chloro-1-naphthyl)-vinyl]-5-methyl-4-piperidinopyridine, 2-[2-(4-chloro-1-naphthyl)ethyl]-5-methyl-4-piperidinopyridine, (Z)-2-[2-(4-fluoro-1-naphthyl)vinyl]-5-methyl-4-piperidinopyridine, 2-[2-(4-fluoro-1-naphthyl)-ethyl]-5-methyl-4-piperidinopyridine, (Z)-2-[2-(4-methoxy-1-naphthyl)vinyl]-5-methyl-4-piperidinopyridine, 2-[2-(4-methoxy-1-naphthyl)ethyl]-5-methyl-4-piperidinopyridine, (Z)-2-[2-(5-methyl-1-naphthyl)vinyl]-5-methyl-4-piperidinopyridine, 2-[2-(5-methyl-1-naphthyl)ethyl]-5-methyl-4-piperidinopyridine, (Z)-2-[2-(5-methoxy-1-naphthyl)vinyl]-5-methyl-4-piperidinopyridine, 2-[2-(5-methoxy-1-naphthyl)ethyl]-5-methyl-4-piperidinopyridine, (Z)-5-methyl-2-[2-(8-methyl-1-naphthyl)vinyl]-4-piperidinopyridine, 5-methyl-2-[2-(8-methyl-1-naphthyl)ethyl]-4-piperidinopyridine, (Z)-2-[2-[2,3-dichlorophenyl)-vinyl]-5-methyl-4-piperidinopyridine, 2-[2-(2,3-dichlorophenyl)ethyl]-5-methyl-4-piperidinopyridine and acid addition salts of the foregoing compounds.

3. A composition in solid dosage form exhibiting anti-ulcer activity and comprising from 5 to 100% by weight of a substituted pyridine derivative of the formula (I) given in claim 1 or a pharmaceutically acceptable acid addition salt thereof, and a pharmaceutically acceptable adjuvant.

4. A composition in liquid dosage form exhibiting anti-ulcer activity and comprising from 0.1 to 10% by weight of a substituted pyridine derivative of the formula (I) given in claim 1 or a pharmaceutically acceptable acid addition salt thereof, and a pharmaceutically acceptable adjuvant.

5. A pharmaceutical composition exhibiting anti-ulcer activity which comprises a therapeutically effective amount of a substitutred pyridine derivative of the formula (I) given in claim 1 or a pharmaceutically acceptable acid addition salt thereof and a pharmaceutically acceptable adjuvant.

6. A method of treating ulcer in a mammal which comprises administering to the mammal a therapeutically effective amount of a substituted pyridine derivative of the formula (I) given in claim 1 or a pharmaceutically acceptable acid addition salt thereof.

7. The method of claim 6 wherein the therapeutically effective amount is in the range of from 0.01 to 20 mg/kg per day.

* * * * *